US012661511B2

(12) United States Patent
Seshan et al.

(10) Patent No.: US 12,661,511 B2
(45) Date of Patent: Jun. 23, 2026

(54) SPINAL CORD STIMULATOR ELECTRODE POSITIONING SYSTEM UTILIZING A MACHINE LEARNING (ML) ALGORITHM

(71) Applicant: SPINESTIM NM LLC, White Plains, NY (US)

(72) Inventors: Karthik Seshan, Ossining, NY (US); Craig Crookston, East Amherst, NY (US); Rahul Gole, Plainsboro, NJ (US); Jeremy Bamford, Mandeville, LA (US); Chris Martin, Ayer, MA (US)

(73) Assignee: SpineStim NM LLC, Ossining, NY (US)

( * ) Notice: Subject to any disclaimer, the term of this patent is extended or adjusted under 35 U.S.C. 154(b) by 755 days.

(21) Appl. No.: 17/723,261

(22) Filed: Apr. 18, 2022

(65) Prior Publication Data

US 2022/0331593 A1 Oct. 20, 2022

Related U.S. Application Data

(60) Provisional application No. 63/175,944, filed on Apr. 16, 2021.

(51) Int. Cl.
*A61N 1/36* (2006.01)
*A61B 5/00* (2006.01)
(Continued)

(52) U.S. Cl.
CPC .......... *A61N 1/36062* (2017.08); *A61B 5/313* (2021.01); *A61B 5/395* (2021.01);
(Continued)

(58) Field of Classification Search
CPC .............. A61N 1/36062; A61N 1/0551; A61N 1/36071; A61N 1/37241; A61N 1/36157; A61N 1/36175; A61N 1/372; A61N 1/0553; A61N 1/0558; A61B 5/313; A61B 5/395; A61B 5/397; A61B 5/7203; A61B 5/7225;
(Continued)

(56) References Cited

U.S. PATENT DOCUMENTS 6,466,817 B1 10/2002 Kaula et al.
7,470,236 B1 12/2008 Kelleher et al.
(Continued)

*Primary Examiner* — Carl H Layno
*Assistant Examiner* — Mary Grace Schlueter
(74) *Attorney, Agent, or Firm* — Caldwell LLC

(57) ABSTRACT

A spinal cord stimulator (SCS) system and method for placing SCS electrodes in a patient for spinal cord stimulation therapy. The SCS system includes a stimulator and a base unit. In conjunction with a machine learning (ML) block, the base unit includes an algorithm module to store and process algorithms for processing data received from recording electrodes placed in a patient's body. The recording electrodes send electromyography (EMG) data to the algorithm module. The algorithm module processes and sends the EMG data to a display device. The displayed data is used, by a surgeon, for lateralization of the SCS electrode. The SCS system further includes algorithms to adjust stimulation parameters related to SCS electrodes based upon the surgeon's workflow. Further, the SCS system allows manual modification of stimulation parameters based upon muscle responses and the EMG data from the recording electrodes.

16 Claims, 21 Drawing Sheets

(51) Int. Cl.

| | |
|---|---|
| *A61B 5/313* | (2021.01) |
| *A61B 5/395* | (2021.01) |
| *A61B 5/397* | (2021.01) |
| *A61N 1/05* | (2006.01) |
| *A61N 1/372* | (2006.01) |

(52) U.S. Cl.
CPC ............ *A61B 5/397* (2021.01); *A61B 5/7203* (2013.01); *A61B 5/7225* (2013.01); *A61B 5/7425* (2013.01); *A61N 1/0551* (2013.01); *A61N 1/36071* (2013.01); *A61N 1/37241* (2013.01); *A61B 5/407* (2013.01); *A61N 1/36157* (2013.01); *A61N 1/36175* (2013.01)

(58) Field of Classification Search
CPC .. A61B 5/7425; A61B 5/407; A61B 2090/376
USPC ............ 607/46, 119, 117; 600/424; 606/129
See application file for complete search history.

(56) References Cited

U.S. PATENT DOCUMENTS

| | | | |
|---|---|---|---|
| 7,522,953 | B2 | 4/2009 | Kaula et al. |
| 8,206,312 | B2 | 6/2012 | Farquhar |
| 8,303,516 | B2 | 11/2012 | Schmitz et al. |
| 8,562,539 | B2 | 10/2013 | Marino |
| 8,801,626 | B2 | 8/2014 | Sun et al. |
| 9,295,401 | B2 | 3/2016 | Cadwell |
| 9,392,953 | B1 | 7/2016 | Gharib |
| 10,039,461 | B2 | 8/2018 | Cadwell |
| 10,258,798 | B2 | 4/2019 | Panken et al. |
| 10,369,364 | B2 | 8/2019 | Moffitt et al. |
| 10,406,369 | B2 | 9/2019 | Jiang et al. |
| 10,441,183 | B2 | 10/2019 | Farquhar |
| 10,588,698 | B2 | 3/2020 | Parker et al. |
| 10,660,567 | B2 | 5/2020 | Cadwell |
| 10,716,509 | B2 | 7/2020 | Kaula et al. |
| 10,814,134 | B2 | 10/2020 | Serrano Carmona et al. |
| 10,842,997 | B2 * | 11/2020 | Moffitt .................. A61N 1/025 |
| 10,912,944 | B2 | 2/2021 | Serrano Carmona et al. |
| 10,918,872 | B2 | 2/2021 | Parker et al. |
| 11,083,887 | B2 * | 8/2021 | Bower ............... A61N 1/37211 |
| 11,337,658 | B2 | 5/2022 | Single et al. |
| 11,497,916 | B2 | 11/2022 | Jiang et al. |
| 11,554,265 | B2 | 1/2023 | Parker et al. |
| 11,648,401 | B2 | 5/2023 | O'Brien et al. |
| 2018/0193651 | A1 * | 7/2018 | Annoni ............. A61N 1/36139 |
| 2019/0275333 | A1 * | 9/2019 | O'Brien ............... A61B 5/4893 |
| 2020/0046265 | A1 * | 2/2020 | Kaifosh ................. A61B 5/388 |
| 2022/0287619 | A1 | 9/2022 | Cleveland et al. |

* cited by examiner

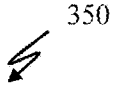

350

| | | 1ST LOCATION ON SPINAL CORD (9TH THORACIC) | 2ND LOCATION ON SPINAL CORD (8TH THORACIC) | 3RD LOCATION ON SPINAL CORD (7TH THORACIC) |
|---|---|---|---|---|
| Patient 1 (Alex) | Electric Current | 0.8 μA | 0.9 μA | 0.7 μA |
| | Pulse Width | 10 Hz | 11 Hz | 8 Hz |
| | SNR | 0.8 dB | 0.9 dB | 0.7 dB |
| | Correlation Coefficient | 0.81 | 0.73 | 0.80 |
| | | | | |
| Patient 2 (Frank) | Electric Current | 0.6 μA | 0.7 μA | 0.9 μA |
| | Pulse Width | 5 Hz | 9 Hz | 10 Hz |
| | SNR | 0.6 dB | 0.7 dB | 0.9 dB |
| | Correlation Coefficient | 0.66 | 0.89 | 0.80 |
| | | | | |
| Patient 3 (Marc) | Electric Current | 0.8 μA | 0.9 μA | 0.7 μA |
| | Pulse Width | 10 Hz | 11 Hz | 8 Hz |
| | SNR | 0.8 dB | 0.9 dB | 0.7 dB |
| | Correlation Coefficient | 0.71 | 0.75 | 0.74 |
| | | | | |
| Patient 4 (Alice) | Electric Current | 0.7 μA | 0.9 μA | 0.6 μA |
| | Pulse Width | 8 Hz | 11 Hz | 10 Hz |
| | SNR | 0.7 dB | 0.7 dB | 0.7 dB |
| | Correlation Coefficient | 0.89 | 0.7 | 0.76 |
| | | | | |
| Patient 5 (June) | Electric Current | 0.8 μA | 0.9 μA | 0.7 μA |
| | Pulse Width | 10 Hz | 11 Hz | 8 Hz |
| | SNR | 0.8 dB | 0.9 dB | 0.7 dB |
| | Correlation Coefficient | 0.77 | 0.63 | 0.78 |

| Position | Active | Refrence |
|---|---|---|
| Config 1 | | |
| Advanced | | |
| 1 | 1 | 2 |
| 2 | 2 | 3 |
| 3 | 3 | 4 |
| 4 | 5 | 6 |
| 5 | 6 | 7 |
| 6 | 7 | 8 |
| Config 2 | | |
| Basic | | |
| 1 | 1 | 2,3,4 |
| 2 | 5 | 6,7,8 |

910

| POSITION 1 | QAUD | AH | TA |
|---|---|---|---|
| Left | 1 | 0 | 0 |
| Right | 0 | 0 | 0 |

| POSITION 2 | QAUD | AH | TA |
|---|---|---|---|
| Left | 1 | 1 | 0 |
| Right | 0 | 0 | 0 |

| POSITION 3 | QAUD | AH | TA |
|---|---|---|---|
| Left | 0 | 1 | 1 |
| Right | 0 | 0 | 0 |

| POSITION 4 | QAUD | AH | TA |
|---|---|---|---|
| Left | 0 | 0 | 0 |
| Right | 1 | 1 | 0 |

| POSITION 5 | QAUD | AH | TA |
|---|---|---|---|
| Left | 0 | 0 | 0 |
| Right | 1 | 1 | 0 |

| POSITION 6 | QAUD | AH | TA |
|---|---|---|---|
| Left | 0 | 0 | 0 |
| Right | 0 | 1 | 1 |

Figure 8C:
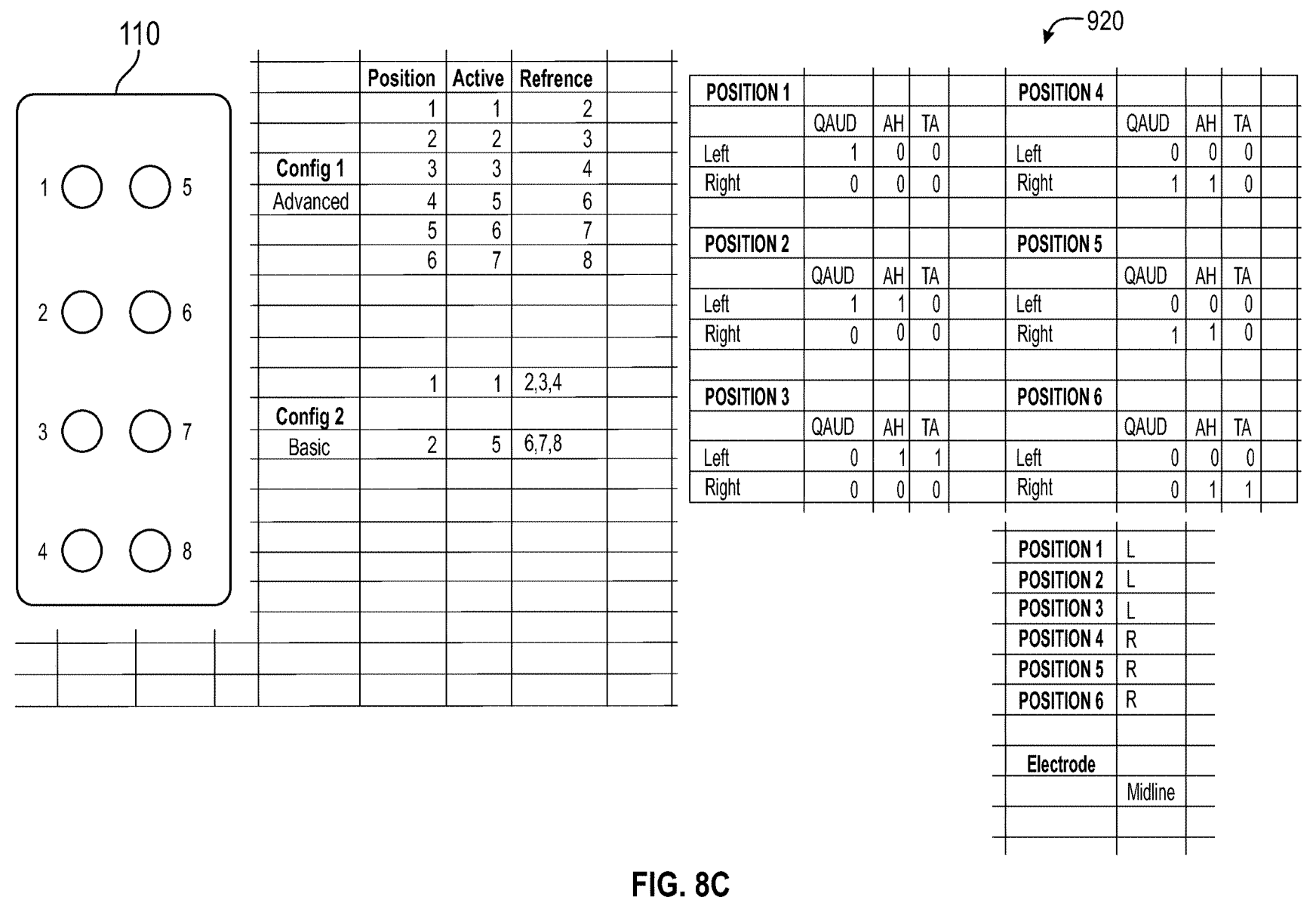

| POSITION 1 | QAUD | AH | TA |
|---|---|---|---|
| Left | 1 | 0 | 0 |
| Right | 0 | 0 | 0 |

| POSITION 2 | QAUD | AH | TA |
|---|---|---|---|
| Left | 1 | 1 | 0 |
| Right | 0 | 0 | 0 |

| POSITION 3 | QAUD | AH | TA |
|---|---|---|---|
| Left | 0 | 1 | 1 |
| Right | 0 | 0 | 0 |

| POSITION 4 | QAUD | AH | TA |
|---|---|---|---|
| Left | 0 | 0 | 0 |
| Right | 1 | 1 | 0 |

| POSITION 5 | QAUD | AH | TA |
|---|---|---|---|
| Left | 0 | 0 | 0 |
| Right | 1 | 1 | 0 |

| POSITION 6 | QAUD | AH | TA |
|---|---|---|---|
| Left | 0 | 0 | 0 |
| Right | 0 | 1 | 1 |

| | |
|---|---|
| POSITION 1 | L |
| POSITION 2 | L |
| POSITION 3 | L |
| POSITION 4 | R |
| POSITION 5 | R |
| POSITION 6 | R |
| Electrode | Midline |

| | Position | Active | Refrence |
|---|---|---|---|
| Config 1 Advanced | 1 | 1 | 2 |
| | 2 | 2 | 3 |
| | 3 | 3 | 4 |
| | 4 | 5 | 6 |
| | 5 | 6 | 7 |
| | 6 | 7 | 8 |
| Config 2 Basic | 1 | 1 | 2,3,4 |
| | 2 | 5 | 6,7,8 |

SPINAL CORD STIMULATOR ELECTRODE POSITIONING SYSTEM UTILIZING A MACHINE LEARNING (ML) ALGORITHM

CROSS REFERENCE TO RELATED APPLICATIONS

The present application claims the benefit of U.S. Provisional Patent Application No. 63/175,944 filed Apr. 16, 2021 entitled "Spinal Cord Stimulator Electrode Positioning System ("SCS-EPS")," the entire disclosure of which is hereby incorporated herein by reference.

FIELD OF THE DISCLOSURE

Exemplary embodiments of the subject disclosure generally relate to a medical device in the field of neuromodulation for assisting in the placement of spinal cord stimulation electrodes, and more particularly related, to the placement of spinal cord electrodes for use in spinal cord stimulation therapy and dorsal root ganglion stimulation, using a machine learning (ML) algorithm.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

Spinal cord stimulation (SCS) therapy is often used to deliver electrical stimulation to activate areas of a spinal cord to treat or manage chronic pain for a patient suffering from failed back surgery syndrome (FBBS) and chronic pain. Typically, SCS therapy makes use of spinal cord stimulators. The spinal cord stimulators are surgical implants used to treat FBBS and chronic pain by modifying nerve activity along the spinal cord to activate areas of the spinal cord, thereby minimizing or masking pain signals from reaching the brain of the patient. Further, SCS therapy allows a surgeon or a doctor to tailor treatment based on the patient's individual needs.

Further, SCS therapy includes two phases, the first phase is a trial phase, and the second phase is a permanent lead placement phase. It can be noted that temporary trials are placed in-office setting using lead electrodes, and the lead electrodes are placed using a small needle. The lead electrodes are further attached to an external battery. After a successful trial, SCS electrodes are placed intraoperatively by performing a small laminectomy to make space to insert and place the electrodes under fluoroscopy inside the patient's body (near the patient's spinal cord). Thus, such accurate placement of the SCS electrode impacts spinal cord stimulation treatment efficacy, and error in that can lead to a failure.

Currently, due to various complexities involved and lack of precision, the SCS electrode placement is less efficient. The SCS electrode placement has a 29% failure rate, and 34% of those failures are due to inadequate pain relief. Suboptimal intraoperative electrode placement is a leading factor. The use of fluoroscopy, anatomical landmarks for the SCS electrode placement, and assuming that spinal column anatomy reflects the anatomical positioning of the spinal cord. However, the center of the spinal cord deviates from the anatomical center of the canal by more than 2 mm, and imaging of the actual spinal cord intraoperatively is expensive and time-consuming due to the use of techniques like O-arm and I-Magnetic resonance imaging (MRI). Further, there is no automated way to assess the functional placement of the electrodes. Further, functional imaging is performed using specialized equipment run by a neurophysiologist with oversight, thus adding to the overall expenditure, labor, and time of the SCS therapy. In addition, there are unwanted electrical signals, which add as noise while monitoring the effects of the SCS electrode placement. Thus, causing a decrease in the signal-to-noise ratio of the system, leading to a decrease in the system's overall efficiency.

Numerous prior arts exist that disclose monitoring the muscle movement, electrodes, and control unit to send the pulses out to the spinal cord. However, there is a need to enhance surgeons' efficiency and safety using pre-clinical and real-time data. Further, there is a need for an automated way to assess the electrodes' functional placement and modify the stimulation and recording parameters. Further, there is a need to allow the surgeon or doctor to view and modify the stimulation parameters. Furthermore, there is a need to improve the signal-to-noise ratio of the system and the overall efficiency of the system. Therefore, there is a need for an improved system to facilitate accurate and efficient placement of spinal cord electrodes for use in spinal cord stimulation therapy and dorsal root ganglion stimulation.

SUMMARY

Various embodiments of the disclosure provide an electrode positioning system that provide for visualization of a Spinal Cord Stimulator (SCS) electrode, spinal cord midline detection, and validation of the placement of the SCS electrode relative to the spinal cord, utilizing a Machine Learning (ML) algorithm. In accordance with an exemplary embodiment of the subject disclosure, an electrode positioning system is provided. The electrode positioning system includes a pulse generator, the pulse generator configured to generate electrical pulse currents based on a parameter selected from a plurality of parameters; a Spinal Cord Stimulator (SCS) electrode, the SCS electrode configured to apply the generated electrical pulse currents at a contact point selected from a plurality of contact points; a recording electrode configured to measure a first electrophysiologic signal triggered by application of the generated electrical pulse currents; an output device configured to indicate the contact point of the SCS electrode relative to a spinal cord; and a base unit, the base unit having: a database, and a Machine Learning (ML) application configured to: receive the measured first electrophysiologic signal, refine the parameter of the SCS electrode for applying the electrical pulse current based on the received first electrophysiologic signal, instruct the pulse generator to generate the electrical pulse currents based on the refined parameter at the contact point where the SCS electrode is located, receive a measured second electrophysiologic signal that is triggered by the application of the electrical pulse currents at the refined parameter by the SCS electrode, determine a correlation coefficient based on a correlation of data previously stored in the database and the second electrophysiological signal, and instruct the output device to indicate locations of the SCS electrode where the determined correlation coefficient is above a predetermined threshold.

In accordance with an aspect of the subject disclosure, the Machine Learning (ML) application is further configured to: compare the determined correlation coefficient with the predetermined threshold; record the determined correlation coefficient in the database as a relevant data and determine if the contact point of the SCS electrode is at a correct location upon determining that the determined correlation coefficient is greater than the predetermined threshold; select another parameter from the plurality of parameters by which the electrical pulse currents are applied based upon which the data is retrieved upon determining that the determined correlation coefficient is less than the predetermined threshold; identify another contact point from the plurality of contact points to place the SCS electrode upon determining that all of the plurality of parameters based on which the determined correlation coefficient of the measured second electrophysiologic signal are compared with the predetermined threshold have been made; and send a notification to the output device to move the SCS electrode to one of indicated locations in which it is determined that the contact SCS electrode is at the correct location.

In accordance with another aspect of the subject disclosure, the output device includes a display for displaying the location of the SCS electrode.

In accordance with still another aspect of the subject disclosure, the measured electrophysiological signal is an electromyography (EMG) signal or a Compound Muscle Action Potential (CMAP).

In accordance with yet another aspect of the subject disclosure, the base unit further includes an amplifier, the amplifier configured to amplify the measured electrophysiologic signal.

In accordance with still another aspect of the subject disclosure, the Machine Learning (ML) application is trained based on a previously obtained electrophysiologic signal, the parameter, or the determined correlation coefficient recorded in the database.

In accordance with yet another aspect of the subject disclosure, the Machine Learning (ML) application communicates with a processor.

In accordance with still another aspect of the subject disclosure, the Machine Learning (ML) application is further configured to filter the retrieved data from the database.

In accordance with another exemplary embodiment of the subject disclosure, an electrode positioning method is provided. The electrode positioning method includes positioning a Spinal Cord Stimulator (SCS) electrode at a spinal cord of a patient; using the electrode positioning system, receiving a first electrophysiologic signal, refining a parameter of the SCS electrode for applying electrical pulse currents based on the received first electrophysiologic signal, instructing a pulse generator to generate the electrical pulse currents based on the refined parameter at the contact point where the SCS electrode is located, receiving a second electrophysiologic signal measured in real time that is triggered by the application of the electrical pulse currents at the refined parameter by the SCS electrode, determining a correlation coefficient based on a correlation of a data previously stored in a database and the second electrophysiological signal, and instructing an output device to indicate locations of the SCS electrode where the determined correlation coefficient is above a predetermined threshold.

In accordance with an aspect of the subject disclosure, the method includes using the electrode positioning system to comparing the determined correlation coefficient with the predetermined threshold; storing the determined correlation coefficient in the database as a relevant data and determining if the contact point of the SCS electrode is at a correct location upon determining that the determined correlation coefficient is greater than the predetermined threshold; selecting another parameter from the plurality of parameters by which the electrical pulse currents are applied based upon which the data is retrieved upon determining that the determined correlation coefficient is less than the predetermined threshold; identifying another contact point from the plurality of contact points to place the SCS electrode, upon determining that all of the plurality of parameters based on which the determined correlation coefficient of the measured second electrophysiologic signal are compared with the predetermined threshold have been made; and sending a notification to the output device to move the SCS electrode to one of the indicated locations in which it is determined that the contact SCS electrode is at the correct location.

In accordance with another exemplary embodiment of the subject disclosure, an electrode positioning system is provided. The electrode positioning system includes a pulse generator, the pulse generator configured to generate electrical pulse currents based on a parameter selected from a plurality of parameters; a Spinal Cord Stimulator (SCS) electrode, the SCS electrode configured to apply the generated electrical pulse currents at a contact point selected from a plurality of contact points; a recording electrode configured to measure a first electrophysiologic signal triggered by the application of the generated electrical pulse currents; an output device configured to indicate the contact point of the SCS electrode relative to a spinal cord; and a base unit, the base unit having: a database, and a Machine Learning (ML) application, wherein the ML application is trained based on the selected parameter and a correlation coefficient based on a correlation of data previously stored in the database and a second electrophysiological signal.

In accordance with an aspect of the subject disclosure, the output device include a display for displaying the location of the SCS electrode.

In accordance with another aspect of the subject disclosure, the measured electrophysiological signal is an electromyography (EMG) signal or a Compound Muscle Action Potential (CMAP).

In accordance with still another aspect of the subject disclosure, the Machine Learning (ML) application communicates with a processor.

In accordance with yet another aspect of the subject disclosure, the Machine Learning (ML) application is trained based on a previously obtained electrophysiologic signal.

In accordance with still another aspect of the subject disclosure, the Machine Learning (ML) application is further configured to filter the retrieved data from the database.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g., boxes, groups of boxes, or other shapes) in the figures represent one example of the boundaries. In some examples, one element may be designed as multiple elements, or those may be designed as one. In some examples, an element shown as an internal component of one element may be implemented as an external component in another and vice versa. Furthermore, elements may not be drawn to scale. Non-limiting and non-exhaustive descriptions are described with reference to the following drawings. The components in the figures are not necessarily to scale, emphasis instead being placed upon illustrating principles.

FIG. 3D illustrates a database for storing information related to different patients, in association with various stimulation parameters, according to an embodiment.

FIG. 8B illustrates a diagram showing datasheets related to lateralization of the SCS electrode, according to another embodiment.

FIG. 8C illustrates a diagram showing datasheets related to lateralization of the SCS electrode, according to another embodiment.

DETAILED DESCRIPTION

Some embodiments of this disclosure, illustrating all its features, will now be discussed in detail. The words "comprising," "having," "containing," and "including," and other forms thereof are intended to be equivalent in meaning and be open-ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context dictates otherwise. Although any systems and methods similar or equivalent to those described herein can be used in the practice or testing of embodiments of the present disclosure, the preferred systems and methods are now described.

Embodiments of the present disclosure will be described more fully hereinafter with reference to the accompanying drawings in which like numerals represent like elements throughout the several figures and in which example embodiments are shown. However, embodiments of the claims may be embodied in many different forms and should not be construed as limited to the embodiments set forth herein. The examples set forth herein are non-limiting examples and are merely examples among other possible examples.

Figure 1:
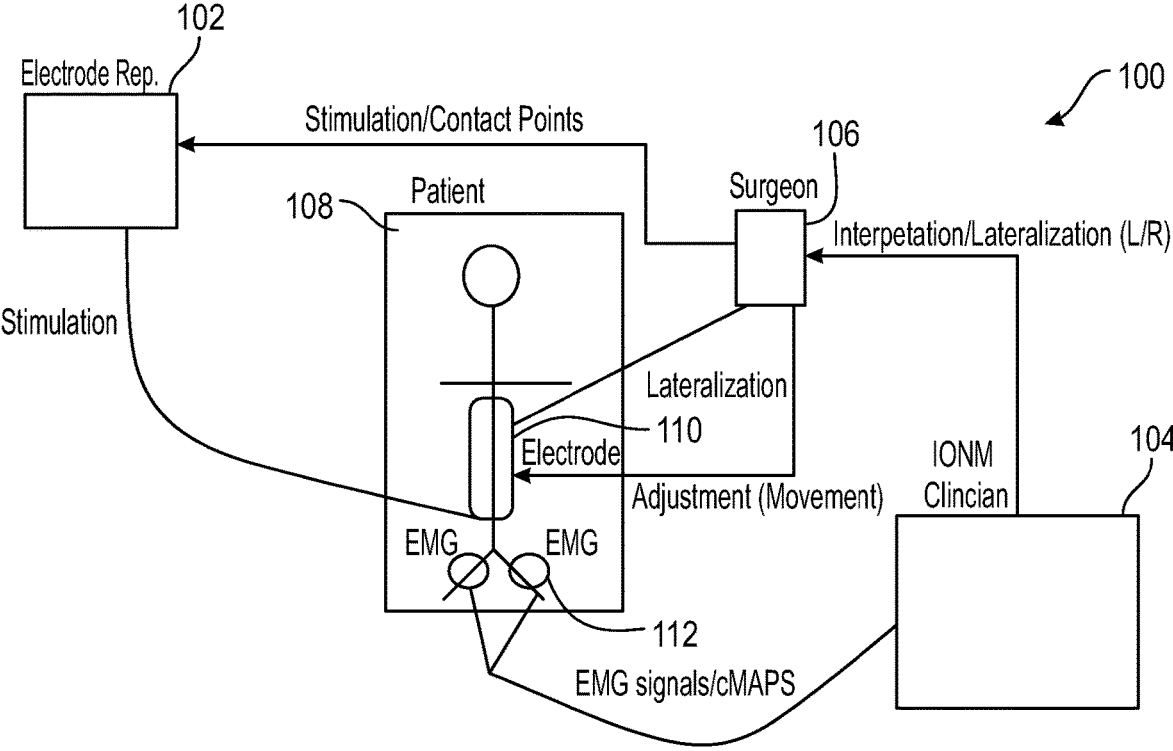
FIG. 1 illustrates a schematic diagram of a medical device system, according to an embodiment.

FIG. 1 illustrates a medical device system 100, according to an embodiment. The medical device system 100 may include an electrode representative 102, an Intraoperative Neuromonitoring (IONM) clinician 104, and a surgeon 106. It can be noted that all may be communicating with each other to treat a patient 108 by accurately placing a spinal cord stimulator (SCS) electrode 110 in the patient's body.

At first, the electrode representative 102 may control the stimulation of the SCS electrode 110 and contact points of the SCS electrode 110. In one embodiment, the SCS electrode 110 may be placed inside the patient's body, such as, but not limited to, along a dorsal column of the spinal cord of the patient 108. Successively, the stimulation of the SCS electrode 110 may generate signals to mask or mitigate pain signals from reaching the brain of the patient 108, suffering from failed back surgery syndrome (FBBS) and chronic pain, based on one or more stimulation parameters. Examples of the one or more stimulation parameters may include but are not limited to pulse width, stimulation intensity, stimulation patter, repetition rate, and frequency. Successively, the patient's body may respond to the stimulation of the SCS electrode 110. The position of the SCS electrodes 110 may also be a stimulation parameter that can be adjusted. In an exemplary embodiment, the SCS electrode 110 may be manufactured by different manufacturers such as but not limited to Medtronic, Boston Scientific, and Abbott Laboratories. Further, the SCS electrode 110 may be either paddle electrodes or cylindrical electrodes. In the case of paddle electrodes, a laminectomy may be required to implant the paddle electrodes in the patient's body. Further, in the case of cylindrical electrodes, the patient 108 might be sedated, as the surgeon 106 slides the SCS electrode 110 along the spinal cord, in a procedure requiring minimal surgical manipulation. Further, there are different types of the orientation of the SCS electrodes 110. It will be apparent to one skilled in the art that the examples mentioned above of SCS electrode 110 have been provided only for illustration purposes, without departing from the scope of the disclosure.

Further, the recording electrodes 112 attached to the patient 108 may be used to measure electromyography (EMG) activity in the patient 108 in a specific area of nerves where the SCS electrode 110 is positioned. In one exemplary embodiment, the recording electrodes 112 may be subdermal recording electrodes 112. In another exemplary embodiment, sticky pads may be used instead of recording electrodes 112 to measure the EMG activity. EMG data refers to any neurophysiologic data that is output by the patient 108 and measured by the recording electrodes 112, in response to the electric current output by the system 100 and applied by the SCS electrode 110. Successively, EMG signals or compound muscle action potential signals (cMAPS) may be sent to the IONM clinician 104. The IONM clinician 104 may assist the surgeon 106 with interpretation or lateralization based on the received signals. In one embodiment, interpretation may refer to a deduced meaning of the signals received from the recording electrodes 112. Further, lateralization may refer to adjusting the SCS electrode 110 in the patient's body. After that, the surgeon 106 may take appropriate action based on the analysis of the signals. After the clinician gives feedback on the SCS electrode 110, the surgeon can do the following things: 1—Physically move the SCS electrode 110 across the spinal cord (lateralization) to get better responses. 2—change which contact points on the SCS electrode 110 are being stimulated to see if you can get better responses. 3—ask the rep to change the stimulation parameters to acquire better signal data. In one case, the surgeon 106 may perform manual adjustment, i.e., movement of the SCS electrode 110 from one position to another. In another case, the surgeon 106 may perform lateralization. In another case, the surgeon 106 may send the stimulation parameters or contact points to the electrode representative 102 to adjust the SCS electrode 110 in the patient's body. Stimulation parameters include adjusting the power, intensity, repetition rate of a current pattern, and frequency on the stimulating SCS electrodes 110.

Figure 2:
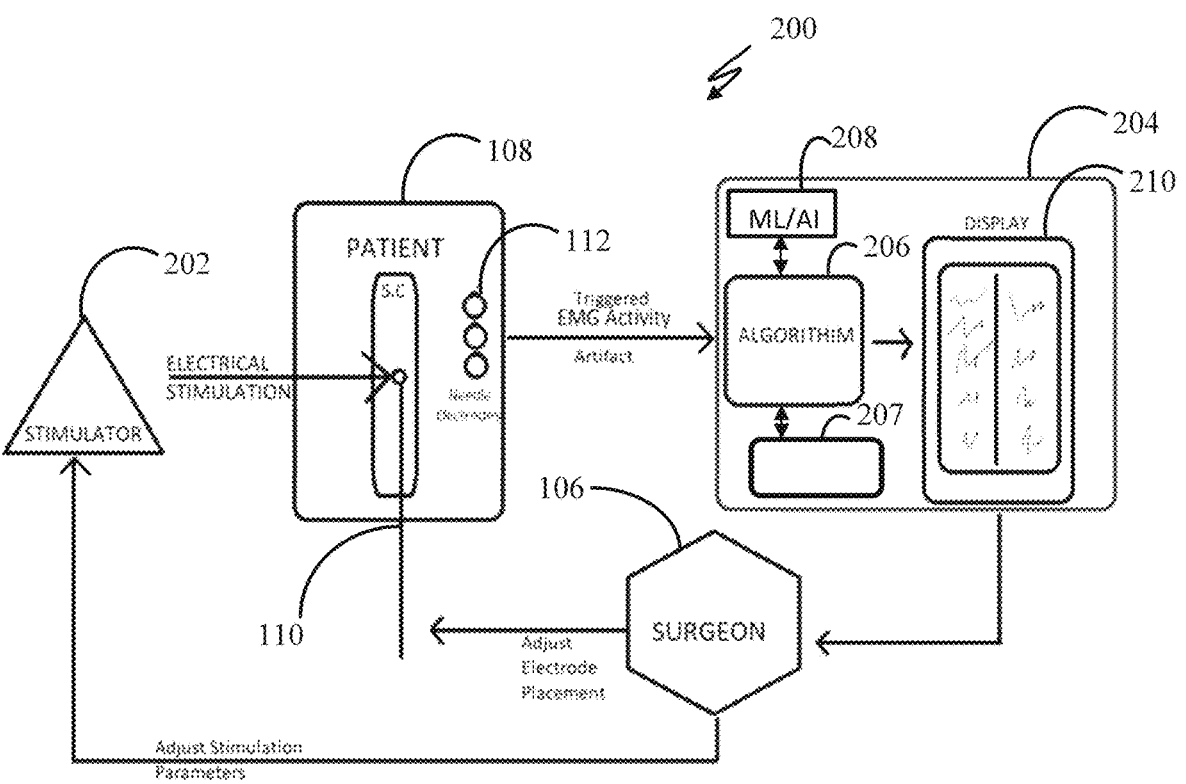
FIG. 2 illustrates a schematic diagram of a spinal cord stimulator (SCS) system to facilitate the placement of spinal cord electrodes, utilizing a Machine Learning (ML) module, according to an embodiment.

FIG. 2 illustrates a schematic diagram of a spinal cord stimulator (SCS) system 200 to facilitate placement of the SCS electrode 110, according to an embodiment. It should be noted that the SCS system 200 may take input from different SCS electrodes 110. The SCS system 200 may automate functional myotomal mapping of the spinal cord to optimize the placement of the SCS electrode 110. The myotomal mapping may be achieved by an algorithm for lateralization, neuromodulation, and interpretation to optimize placement of the SCS electrode 110, wherein the algorithm for lateralization may be for placement of the SCS electrode 110 at the center of the spinal cord. Further, neuromodulation may be for modulation or adjustment of the nerve parameters by delivering electrical impulse directly to a target area, and interpretation may be for processing and visualization of placement of the SCS electrode 110.

The SCS system 200 may allow the surgeon 106 to accurately place the SCS electrode 110 inside the patient's body to maximize its effectiveness on mitigation and mediation of pain in the spinal cord of the patient 108. The SCS system 200 may be a surgeon-controlled standalone unit that guides the surgeon 106 in the placement of the SCS electrode 110 using neurophysiological data to optimize the position of the SCS electrode 110 and stimulation level for the SCS electrode 110, to optimize pain control of the patient 108. Further, the SCS system 200 may allow the surgeon 106 to easily modify and optimize stimulation and position of the SCS electrode 110 in substantially real-time without the need for additional clinical resources that are often costly and time-consuming. Further, the SCS system 200 may reduce risk by allowing the patient 108 to be placed under general anesthesia during the initial placement of the SCS electrodes 110. Such SCS system 200 may limit exposure of a patient's spinal cord during the initial placement of the SCS electrode 110 on the spinal cord.

As shown in FIG. 2, the SCS system 200 may include a stimulator 202 and a base unit 204 (e.g., a device, a receiver, or an amplifier unit including an amplifier). In one embodiment, the stimulator 202 may be configured as a pulse generator. The stimulator 202 may be in communication with the SCS electrode 110. Further, the stimulator 202 may be operable to generate electrical pulses based on a variety of predetermined parameters provided by the surgeon 106 and based on the individual needs of the patient 108. In one embodiment, the predefined parameters may be referred to as stimulation parameters. The stimulation parameters may include but are not limited to pulse width, stimulation intensity, repetition rate, and frequency. The position of the SCS electrodes 110 may also be a stimulation parameter that can be adjusted. It should be noted that the electrical pulses may be used to negate and/or mitigate pain in targeted regions of the patient 108, for example, in the lower back and legs of the patient 108.

Successively, the stimulator 202 may send the electrical pulses to the SCS electrode 110 to reduce and control the pain. Further, the recording electrodes 112 attached to the patient 108 may measure EMG data or activity in the patient 108 in a specific area of nerves where the SCS electrode 110 is positioned. Further, the EMG activity may be triggered by nerve activation resulting from electrical pulses sent to the SCS electrode 110. In one exemplary embodiment, the recording electrodes 112 may be subdermal recording electrodes 112. In another exemplary embodiment, sticky pads may be used instead of recording electrodes 112 to measure the EMG activity. Further, the SCS system 200 includes the base unit 204 that amplifies and analyzes the EMG data from the recording electrodes 112. Further, the base unit 204 may detect the type of the SCS electrode 110, based at least on different parameters such as the manufacturing company and pin configuration of the SCS electrode 110.

In addition, EMG activity may be measured via EMG signals in the patient's body. Further, when passing through various tissues inside the patient's body, the EMG signal may acquire various noises, artifacts, or unwanted signals. The noises may affect the quality of the EMG signal, thus causing difficulty in the analysis of the EMG signal. To overcome the noises, the EMG signal may undergo a filtration process. It can be noted that such use of a filtration process may improve the signal-to-noise ratio of the EMG signal by reducing the noise in the EMG signal. In one embodiment, the filtration process may be carried out using one filter or a combination of filters, but not limited to, low pass filter, high pass filter, and notch filter. Such filtering may maximize signal clarity and reduce the SCS system 200 background noise while determining an optimal threshold.

Further, the base unit 204 may include an algorithm module (e.g., processor) 206 coupled to a machine learning (ML) module (e.g., algorithms and/or models) 208 and a display device 210. The algorithm module 206 may process the EMG data using the ML module 208 to filter the EMG data. The EMG data is filtered to reduce the impact of artifacts generated by the stimulator 202. It can be noted that the EMG data corresponds to real-time data. As discussed above, it can be noted that such use of a filtration process may improve the signal-to-noise ratio of the EMG signal by reducing the noise in the EMG signal. In one embodiment, the filtration process may be carried out using one filter or combination of filters, including low pass filter, high pass filter, and notch filter. Such filtering may maximize signal clarity and reduce the SCS system 200 background noise while determining an optimal threshold.

The ML module 208 may be a program stored in memory on a local computing device, such as a laptop, smartphone, tablet, computer, smart speaker, or dedicated medical device. The ML module 208 may also be remote and in communication via a cloud or a communication network that may be wired and/or wireless. The communication network, if wireless, may be implemented using communication techniques such as visible light communication (VLC), worldwide interoperability for microwave access (WiMAX), long term evolution (LTE), wireless local area network (WLAN), infrared (IR) communication, public switched telephone network (PSTN), radio waves, or other communication techniques that are known in the art. The communication network may allow ubiquitous access to shared pools of configurable system resources and higher-level services that can be rapidly provisioned with minimal management effort, often over the internet, and relies on sharing resources to achieve coherence and economies of scale, like a public utility. In contrast, third-party clouds allow organizations to focus on their core businesses instead of expending resources on computer infrastructure and maintenance.

Further, the algorithm module 206 may access pre-clinical data related to the SCS electrode 110 and the recording electrodes 112. Further, the algorithm module 206 may compare the pre-clinical data to the real-time data using the ML module 208. Based on the comparison of the pre-clinical data to the real-time data, the algorithm module 206 using the ML module 208 may automatically adjust the stimulation parameters and the position of the SCS electrode 110. In one embodiment, the algorithm module 206 may store the pre-clinical and real-time data in a database (not shown). Further, the ML module 208 may facilitate optimizing a plurality of factors to produce an optimal response that considers the signal-to-noise ratio. The plurality of factors may include but are not limited to pulse width, stimulation intensity, repetition rate, and frequency. In addition, this may include the number of pulses in a pulse train, constant hertz level, variable hertz level, etc. Further, the stimulation waveform phase and type such as monophasic or biphasic waveforms may also factor into the ML algorithm. Such usage of the ML module 208 may predict and optimize the suggestions, change in stimulation parameters, and spinal recording parameters to be displayed at the display device 210 for the surgeon 106. Recording parameters include adjusting gains and filtering of signals with respect to the recording electrodes 112.

It can be noted that such use of the ML module 208 may utilize neural networks, machine learning, and artificial intelligence for the placement of SCS electrode 110 in a patient. Further, the ML module 208 may facilitate self-modulation of parameters associated with the SCS system 200, based on real-time data measurements. The ML module 208 may utilize neural networks, machine learning, and artificial intelligence to place the SCS electrode 110 in the patient's body. The ML module 208 may operate the SCS system 200. The detailed description of the ML module 208 will be described later in conjunction with FIG. 3A.

In one embodiment, the display device 210 may correspond to output devices including, but not limited to, video displays, graphical displays, speakers, headphones, inkjet printers, laser printers, and 3D printers. It can be noted that the function of the display device 210 may indicate to the surgeon 106 related to the EMG data. In another embodiment, the display device 210 may correspond to an input/output device like a touch screen, capable of receiving inputs from the surgeon 106, such as selecting the desired option, at the display device 210. In one embodiment, the SCS electrode 110 may be connected to the base unit 204 via an adapter, as explained in conjunction with FIG. 4.

Further, the display device 210 may be connected to an external screen or monitor to visualize the location of the SCS electrode 110, based on the EMG activity from the algorithm module 206. In one embodiment, the external screen or monitor may display the relative location of SCS electrode 110 on the spinal column based on EMG activity in real-time. The visualization of the SCS electrode 110 may vary based on the vendor and type of SCS electrode 110 utilized. Additionally, the external display may provide a visual representation of the dermatomes and/or myotomes, i.e., areas of skin/muscles, that the SCS electrode 110 is activating. It can be noted that the SCS system 200, via the display device 210, may receive feedback for positioning the SCS electrode 110 in real-time.

In another embodiment, the displayed data may be used by the surgeon 106 to adjust parameters related to the SCS electrode 110 and the location of the SCS electrode 110. In one embodiment, the parameters related to the recording electrodes 112 may be adjusted based on workflow or experience of the surgeon 106, i.e., doctor (i.e., what the doctor's experience is doing). In one embodiment, the parameters related to the recording electrodes 112 may be adjusted based on neurophysiology (i.e., needles are in the right place, but nerves don't react) or placement of the recording electrodes 112 workflows or experience of the surgeon 106. Further, the parameters related to the recording electrodes 112 may be modified manually by the surgeon 106, based upon muscle responses and data from the recording electrodes 112. In one embodiment, the algorithm module 206 may allow the surgeon 106 to manually modify stimulation parameters and position of the SCS electrode 110, based on the lateral location of the SCS electrode 110 displayed by the display device 210.

There are various scenarios of the algorithm module 206 for adjusting the stimulation parameters applied to the SCS electrode 110. In one exemplary scenario, the algorithm module 206 may be configured to adjust the parameters applied to each SCS electrode 110 based upon what is happening in the workflow of the surgeon 106 or doctor (i.e., what the doctor is doing during a procedure). In a first scenario, the algorithm module 206 may run a gamut of stimulation parameters applied to the SCS electrode and monitor any changes in the EMG response to the SCS electrode 110 stimulation. When no response is monitored in the EMG activity, a "no response" record is recorded in the system 200, the parameter may be adjusted (e.g., current may be increased), and the sequence may run again, to ensure the presence of the EMG response. Further, the response may be logged for any overlap among the EMG data. The logged data may be stored in a historical database 207 with annotated tags for the response as historical data. Further, a correlation of the historical data and real-time data may be stored in the historical database 207. The historical database 207 may include information related, but not limited to, a good correlation and a poor correlation relative to the real-time data and the historical data.

In another exemplary scenario, the algorithm module 206 may be configured to perform an impedance check on the SCS electrode 110. This ensures that the SCS electrode 110 is making proper contact with actual tissue. Here, a pulse is applied to the SCS electrode 110, and impedance is recorded by the recording electrode 112. If no impedance is recorded, then it may be gathered that the SCS electrode 110 is not properly contacting the tissue, such as a spinal cord. Alternatively, it may also be the case that the recording electrode 112 is not properly contacting the muscles for recording the impedance.

Figure 5A:
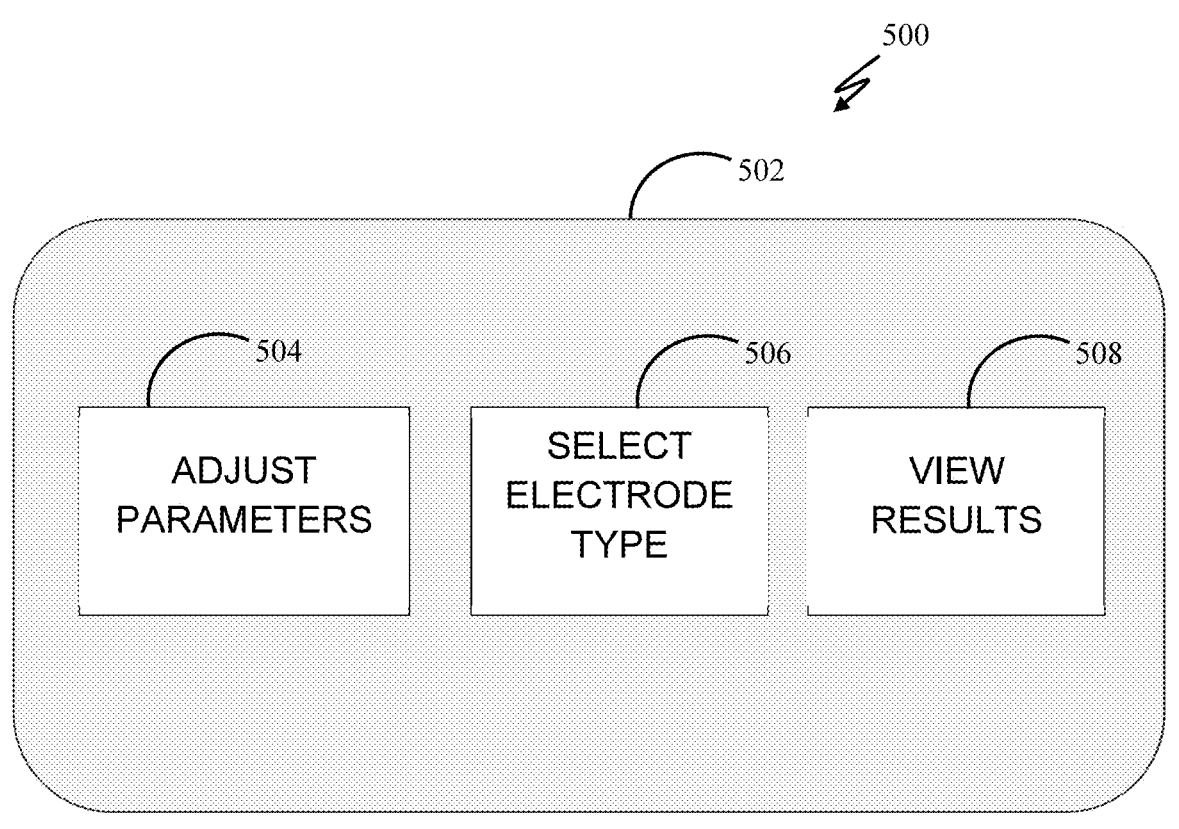
FIG. 5A illustrates a block diagram 500 showing a user interface (UI) for allowing a surgeon to input stimulation parameters in the SCS system, according to an embodiment.
Figure 5B:
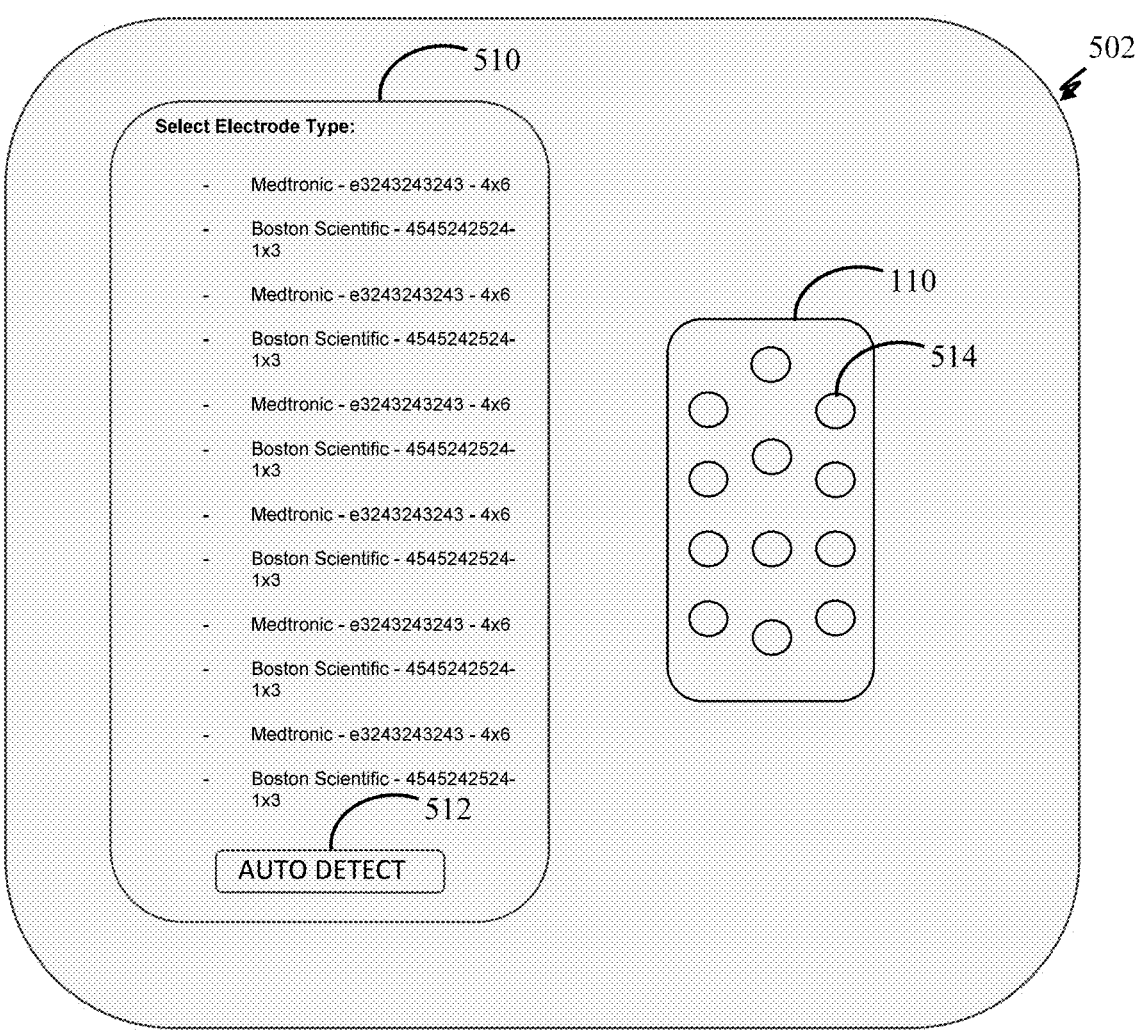
FIG. 5B illustrates a block diagram showing an exemplary UI, for allowing the surgeon to select electrode type in the SCS system, according to an embodiment.

In one embodiment, the base unit 204 may include a User Interface (UI) to manually allow the surgeon 106 to enter the stimulation parameters to modify the placement of the SCS electrode 110 based upon muscle responses and data from the subdermal recording electrode 112, as explained in conjunction with FIG. 5A and FIG. 5B. Further, the UI may be used to manually allow stimulation parameters and modifying the spinal recording parameters based on muscle responses and data from a subdermal recording electrode 112 or impedance. In one embodiment, the surgeon 106 may adjust the placement of the SCS electrode 110 and not adjust the stimulation parameters. In another embodiment, the surgeon 106 may adjust the stimulation parameters and not adjust SCS electrode 110 placements without departing from the scope of the disclosure.

Figure 3A:
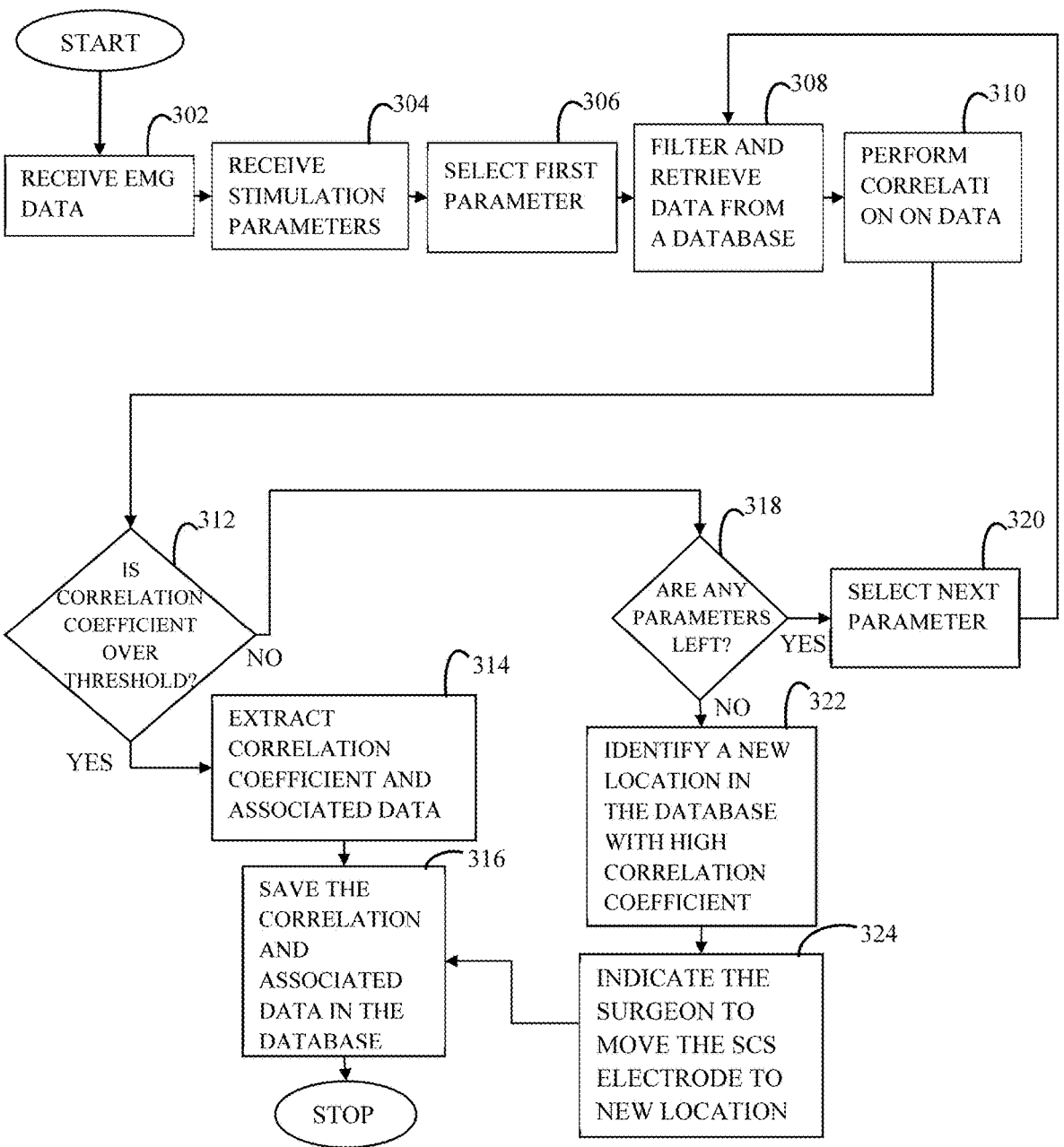
FIG. 3A illustrates a method 300 showing an operation of the ML module, according to an embodiment.

FIG. 3A illustrates a method 300 showing an operation of the ML module 208, according to an embodiment. It should also be noted that in some alternative implementations, the functions noted in the blocks may occur out of the order noted in the drawings. For example, two blocks are shown in succession in FIG. 3A may be executed substantially concurrently, or the blocks may sometimes be executed in the reverse order, depending upon the functionality involved. In addition, the process descriptions or blocks in flow charts should be understood as representing decisions made by a hardware structure such as a state machine. The flowchart 300 starts at step 302 and proceeds to step 320.

The process begins with the ML module 208 that receives EMG data from the algorithm module 206, in response to an input of stimulation parameters to the SCS electrode 110, at step 302. For example, Alex is suffering from back pain, and Dr. T. is operating on Alex. The SCS electrode 110 is initially implanted at the 9$^{th}$ thoracic level of the spinal cord of Alex. Further, the recording electrodes 112 collect real-time data related to Alex, like EMG activity—fibrillation along with an SNR value. For example, an SNR value of 0.8 dB is received as EMG data when the SCS electrode 110 is placed at the 9$^{th}$ thoracic of the spinal cord of Alex. Successively, the ML module 208 receives the stimulation parameters or information associated with the self-modulation of parameters associated with the SCS system 200, from the algorithm module 206, at step 304. For example, an electric current of 0.8 μA and a pulse width of 10 Hz is applied to the SCS electrode 110 inserted at the 9$^{th}$ thoracic of the spinal cord of Alex. Successively, a first stimulation parameter is selected at step 306. For example, the first parameter is selected, which in this example is the electric current of 0.8 μA applied to the SCS electrode 110. Successively, the ML module 208 filters and retrieves data 350 (shown in FIG. 3D) from the historic database 207 related to at least one characteristic of the SCS electrode 110 for respective patients, at step 308. In one embodiment, the ML module 208 filters data associated with the self-modulation of parameters associated with the SCS system 200 to create a subset of data for the characteristic. For example, the ML module 208 filters the data for electric current of 0.8 μA at the 9$^{th}$ thoracic of the spinal cord, as a subset of data corresponding to 1$^{st}$ location on the spinal cord (9$^{th}$ thoracic) is filtered from the data 350 shown in FIG. 3D. It can be noted that the data 350 includes information corresponding to the 9$^{th}$ thoracic on the spinal cord, for different patients—Alex (electric current—0.8 μA, pulse width—10 Hz, and SNR—0.8 dB), Frank (electric current—0.6 μA, pulse width—5 Hz, and SNR—0.6 dB), Marc (electric current—0.8 μA, pulse width—10 Hz, and SNR—0.8 dB), Alice (electric current—0.7 μA, pulse width—8 Hz, and SNR—0.7 dB), and June (electric current—0.8 μA, pulse width—10 Hz, and SNR—0.8 dB). Further, the subset of the filtered data includes records for electric current—0.8 μA and location as 9$^{th}$ thoracic on the spinal cord.

Figure 3B:
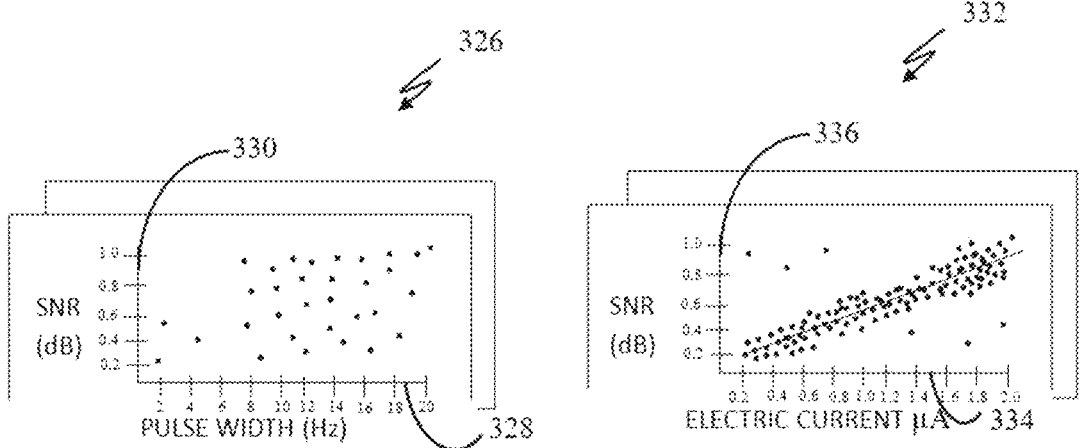
FIG. 3B illustrates a graph showing outcomes of the ML module, according to an embodiment.
Figure 3C:
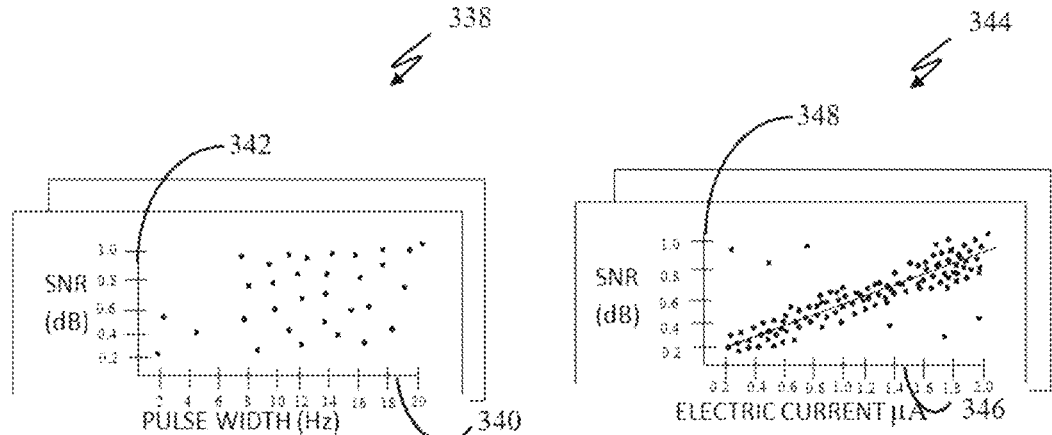
FIG. 3C illustrates another graph showing outcomes of the ML module, according to an embodiment.

Successively, the ML module 208 may perform correlations on the filtered data of the SCS electrode 110 with the real-time data collected from the recording electrodes 112 at step 310. For example, the ML module 208 performs correlations of the electric current values of 0.8 μA with an SNR value of 0.8 dB at the 9$^{th}$ thoracic of the spinal cord of Alex, as shown in FIG. 3B and FIG. 3C. The correlated data involving Alex, with the SCS electrode 110 at the 9$^{th}$ thoracic of his spinal cord, has a correlation coefficient of 0.81. Further, the correlation coefficient is determined in relation to a predetermined threshold at step 312. For example, the correlation coefficient of 0.81 with the electric current value of 0.8 μA is determined in relation to a predetermined threshold of 0.75.

If the correlation coefficient is above the predetermined threshold, the correlation coefficient is deemed highly relevant, and the correlation coefficient is extracted at step 314. For example, the correlation coefficient of 0.81 for the SCS electrode 110 placed at the 9$^{th}$ thoracic of Alex's spinal cord is above the threshold of 0.75, which is extracted. After that, when it is determined that the correlation coefficient is highly relevant, then the SCS electrode 110 is at a correct location, such as in this example, the 9$^{th}$ thoracic of the spinal cord of Alex. Further, the correlated coefficient is saved in the data 350, at step 316. In this example, the correlation coefficient 0.81 for the SCS electrode 110 placed at the 9$^{th}$ thoracic of Alex's spinal cord and the associated electric current value of 0.8 μA and the SNR value of 0.8 dB is saved in the data 350.

In another case, if the correlation coefficient is lower than the predetermined threshold at step 312, then the ML module 208 checks if there are any remaining parameters at step 318. In one case, if there is any remaining parameter, the ML module 208 may select the next parameter, at step 320, to repeat steps 308 to 316, to find a suitable location for the placement of the SCS electrode 110. The next parameter may be but is not limited to impedance, pulse width, and electrical current. For this example, the next parameter is the pulse width. After that, the correlations between the parameters and the received signal data may be performed on the rest of the electrical current signal parameters applied to the SCS electrode 110, which may include impedance, pulse width, and electrical current, and coefficient coefficients may be output. In another case, at step 318, if it is determined that there are no remaining parameters, then the ML module 208 identifies a new SCS electrode 110 location from the data 350 stored in the historical database 207 where a relatively high correlation coefficient has been determined, at step 322. The location may be inputted by a physician as preferred locations, or SCS electrode 110 contact points that have be pre-identified by the system 200 as triggering relatively high correlation coefficients from signals (e.g., EMG patterns) recorded by the recording electrodes 112 and pre-stored as data 350 in the historical database 207. The desired output may be EMG patterns related to the current inputs by the SCS electrode 110 operating at certain stimulation parameters at a given location. That is, in one embodiment, In one embodiment the physician may provide some preferred starting points. Optionally after the system has been used enough times, the points with the highest correlation coefficients could be identified in the database 350.

In another embodiment, the new location may be identified where inputs or stimulation parameters are correlated above a threshold with the desired output. The data 350 stored within the database 207 would have a number of datapoints of previous correlations associated with parameter inputs and SCS electrode 110 locations. Either the system 200 or the physician may identify the physician's preference or an SCS electrode 110 location that is highly correlated with the desired output. In another embodiment, if a location is identified on the spinal cord for placing the SCS electrode 110 that connects the nerves to the location to be treated, then a variety of inputs and outputs may be correlated. For example, the electric current and the SNR value have a high correlation coefficient of 0.80 at the $7^{th}$ thoracic of the spinal cord will be identified. Successively, the identified new location may be indicated to the surgeon 106 for moving the SCS electrode 110 to the new location at step 324. The input parameters (in this case a given electric current and snr value) is highly correlated with the desired EMG output. The next location is either selected by the physician based on their preferences or a high correlation coefficient in the data 350. For example, the $7^{th}$ thoracic of the spinal cord of Alex is indicated to Dr. T for moving the SCS electrode 110. Successively, the ML module 208 moves to step 316, to save the correlation and associated data 350 in the historical database 207 and end the process.

In one embodiment, the EMG data and the stimulation parameters may be displayed on the display device 210 for the surgeon 106. The display device 210 may be configured to display the compared data such as, but not limited to, the EMG activity, position of SCS electrode 110, and the stimulation parameters that were used at each contact point for the SCS electrode 110 for the surgeon 106. The display device 210 displays the difference in the real-time data, the pre-clinical data, and the current lateral position of the SCS electrode 110. The stimulation parameters may include but are not limited to pulse width, stimulation intensity, repetition rate, and frequency. The surgeon 106 may view the processed data so that the surgeon 106 can take the appropriate action. The action may be, but not limited to, changing the position of the SCS electrode 110, changing stimulation parameters related to the recording electrodes 112, and changing electrode type. It can be noted that such use of the algorithm module 206 may optimize the placement of the SCS electrode 110.

FIG. 3B provides an illustration of an example of the ML module 208 and the resulting correlations when the SCS electrode 110 is placed at the $7^{th}$ thoracic of the spinal cord of Alex. FIG. 3B shows a graph 326 with SCS modulation parameter, i.e., pulse width applied to the SCS electrode 110, on the X-axis, as shown by 328, with EMG data, i.e., Signal to Noise ratio (SNR) on the Y-axis, as shown by 330, which is not correlated to each other. Further, FIG. 3B shows a graph 332 with SCS modulation parameter, i.e., the electric current applied to the SCS electrode 110, on the X-axis, as shown by 334, with EMG data, i.e., Signal to Noise ratio (SNR) on the Y-axis, as shown by 336, which are highly correlated to each other.

FIG. 3C provides an illustration of an example of the ML module 208 and the resulting correlations when the SCS electrode 110 is placed at the $9^{th}$ thoracic of the spinal cord of Alex. FIG. 3C shows a graph 338 with SCS modulation parameter, i.e., pulse width applied to the SCS electrode 110, on the X-axis, as shown by 340, with EMG data, i.e., Signal to Noise ratio (SNR) on the Y-axis, as shown by 342. Further, FIG. 3C shows a graph 344 with SCS modulation parameter, i.e., an electric current applied to the SCS electrode 110, on the X-axis, as shown by 346, with EMG data, i.e., Signal to Noise ratio (SNR) on the Y-axis, as shown by 348. It can be noted that among FIG. 3B and FIG. 3C, FIG. 3C (at $9^{th}$ thoracic of the spinal cord of Alex) reflects a higher correlation coefficient between the two examine parameters, with high correlation coefficient of 0.81, as compared to the ones reflected in FIG. 3B (at $7^{th}$ thoracic of the spinal cord of Alex), with the correlation coefficient of 0.80. Typically, a predetermined threshold, such as greater than 0.75, for a relevant correlation coefficient may be used. Correlation coefficients may also be compared relative to one another, with the more correlated parameters chosen.

Figure 4:
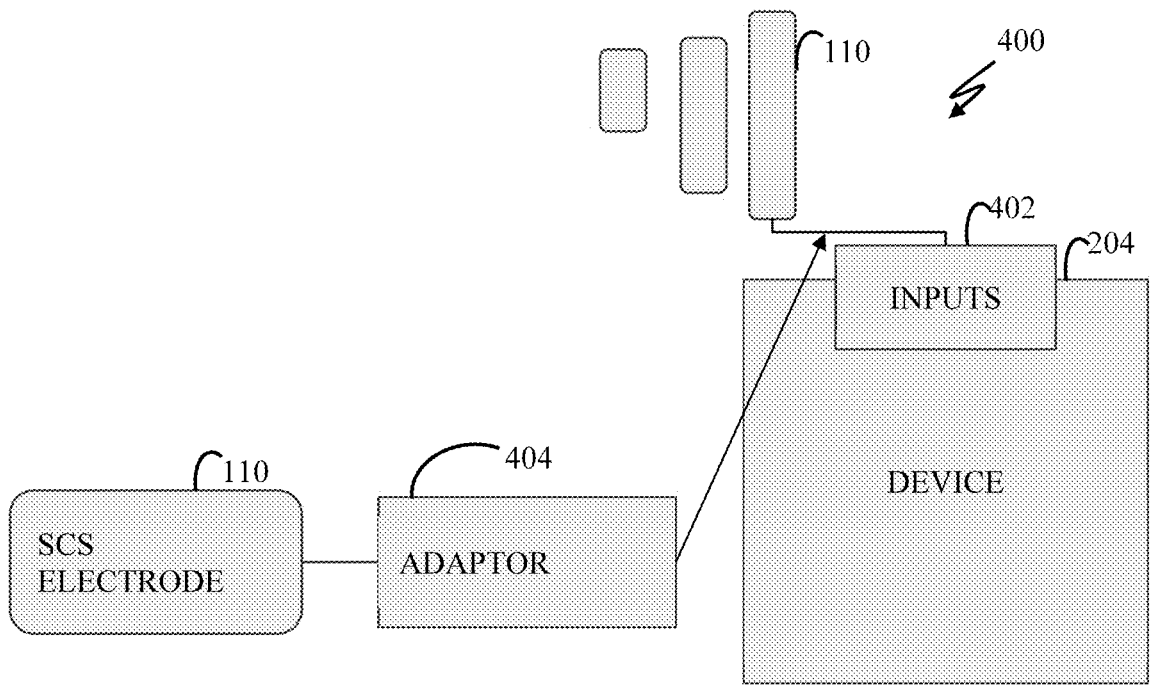
FIG. 4 illustrates a block diagram showing electrode connections in the SCS system using an adaptor, according to an embodiment.

FIG. 4 illustrates a block diagram 400 showing SCS electrode 110 connection in the base unit 204, according to another embodiment. In one embodiment, when the SCS electrode 110 is directly compatible with the base unit 204, then the SCS electrode 110 is connected directly to the base unit 204 of the SCS system 200 via inputs 402. It should be noted that once the SCS electrodes 110 are in the base unit 204 of the SCS system 200, it may initialize. In another embodiment, when the SCS electrode 110 is not directly compatible with the base unit 204, then the SCS electrode 110 is connected indirectly to the base unit 204, using an adaptor 404 (i.e., proprietary connectors), as shown in FIG. 4.

As shown in FIG. 5A, the base unit 204 may include a user interface (UI) 502 to manually allow the surgeon 106 to enter the stimulation parameters to modify the placement of the SCS electrode 110 based upon muscle responses and data from the recording electrode 112. It can be noted that the recording electrodes 112 may be used to take the EMG data associated with patient 108. The recording electrodes 112 may take the EMG data associated with the patient 108 in a specific target area of the nerves where the SCS electrodes 110 are positioned. In one embodiment, the EMG activity may be triggered by muscle contraction resulting from electrical pulses sent to the SCS electrode 110. In one embodiment, the UI 502 may include a first button, 504, for adjusting parameters. The parameters may be stimulation parameters or spinal recording electrode 112 parameters. In an exemplary scenario, a user interface (UI) may be used to manually allow stimulation parameters and modifying the spinal recording parameters based on muscle responses and data from a subdermal electrode or impedance. In another embodiment, the UI 502 may include a second button 506 to select a particular electrode type, as shown in FIG. 5B. In another embodiment, the UI 502 may include a third button 508 to view results corresponding to changes in the stimulation parameters, based on the muscle responses and the EMG activity received from the recording electrodes 112.

FIG. 5B illustrates an exemplary user interface (UI) 502 showing an SCS electrode 110 selection page 510 displayed for the surgeon 106. It can be noted that once an SCS electrode 110 is selected (as shown in FIG. 5A), the SCS system 200 initializes a protocol to detect or select an SCS electrode 110. In one embodiment, the SCS electrode 110 selection page 510 may display a list of predefined SCS electrode 110s used. In an exemplary embodiment, the list of pre-defined SCS electrode 110s includes Medtronic— e3243243243—4×6, Boston Scientific—4545242524—1× 3, Medtronic—e3243243243—4×6, Boston Scientific— 4545242524—1×3, Medtronic—e3243243243—4×6, Boston Scientific—4545242524—1×3, Medtronic— e3243243243—4×6, Boston Scientific—4545242524—1× 3, Medtronic—e3243243243—4×6, Boston Scientific— 4545242524—1×3, Medtronic—e3243243243—4×6, and Boston Scientific—4545242524—1×3. Further, the UI 502 may request the surgeon 106 select an SCS electrode 110 from the list. Further, the SCS electrode 110 selection page 510 may include an auto-detect button 512, facilitating automatic detection of the type of the SCS electrode 110. Based on the selection or detection of the SCS electrode 110, the SCS system 200 may initialize the SCS electrode 110 type. Successively, based on the SCS electrode 110 type, the SCS system 204 may recognize the orientation of contact points 514 of the SCS electrode 110, as shown in FIG. 5B.

Figure 6A:
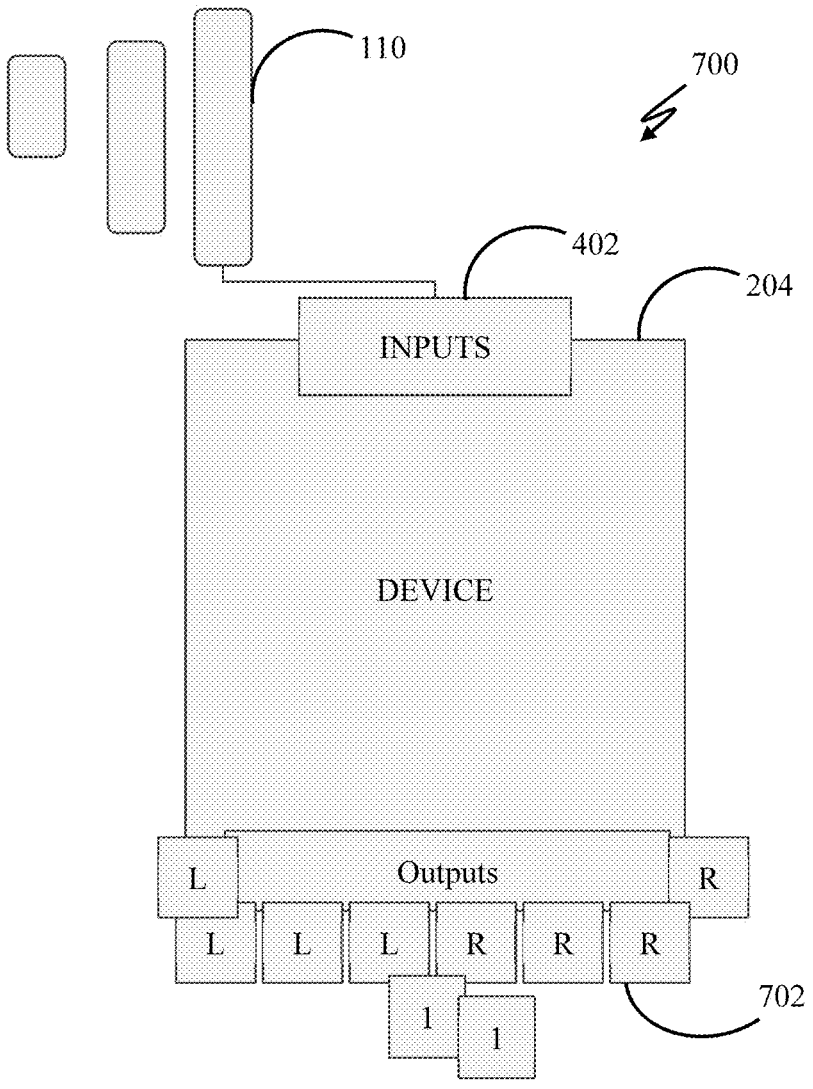
FIG. 6A illustrates a block diagram showing an exemplary scenario of the SCS system, according to an embodiment.
Figure 6B:
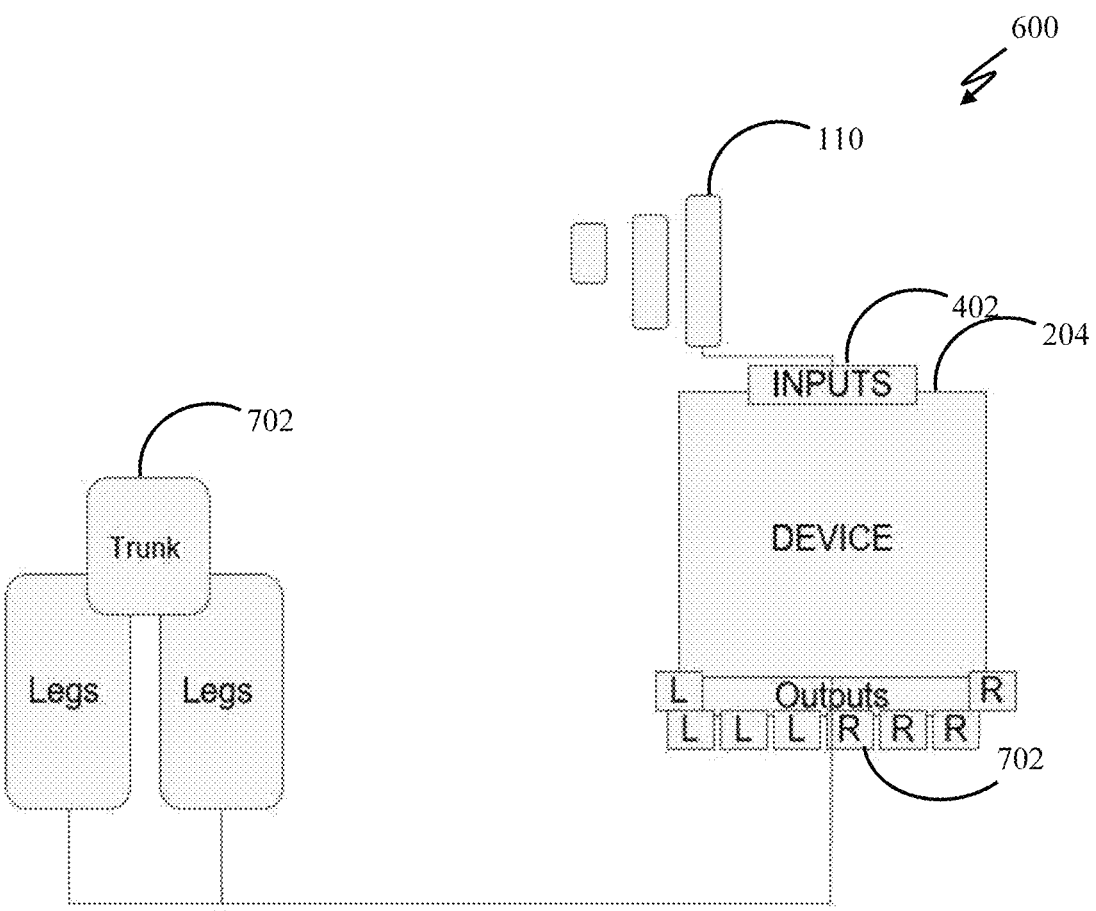
FIG. 6B illustrates a block diagram 600 showing another exemplary scenario of the SCS system, according to an embodiment.

FIG. 6A and FIG. 6B illustrate a block diagram 700 showing an exemplary setup of the SCS system 200, according to an embodiment. The SCS electrode 110 may be connected to the SCS system 200 through the inputs 402 of the base unit 204 (shown as a device 204 in FIG. 6A). Further, the recording electrodes 112 may hook up to the patient 108 to the appropriate muscles. Further, the surgeon 106 may prepare and finalize the setup by confirming the connections complete and proper. Successively, the patient 108 may be given anesthesia, keeping track of the degree of muscle relaxation of the patient 108 by interpreting muscle response during testing of SCS electrode 110 may be made. Further, the SCS system 200 may be using the bi-polar recoding through eight channels machines to collect one or more EMG data. In one exemplary embodiment, the eight-channel machine may include recording electrodes 112. The SCS system 200 may take in Bilateral PSOAS, QUAD, TA, AH EMG Signals. In one embodiment, the machine may take in standard EMG inputs. It should be noted that off-the-shelf needles may be used. The SCS system 200 may use EMG recording electrodes 112 without departing from the scope of the disclosure. Further, other ends 702 of eight channels machines may be connected to muscles of the patient 108, as shown in FIG. 6B. In one embodiment, the eight-channeled machine may be connected to at least the legs and trunk of the patient 108, as shown in FIG. 6B. It can be noted that the surgeon 106 may confirm if all the connections are complete and proper. Successively, display 208 in the base unit 204 may be activated to show the EMG data received from the recording electrode 112.

Figure 7:
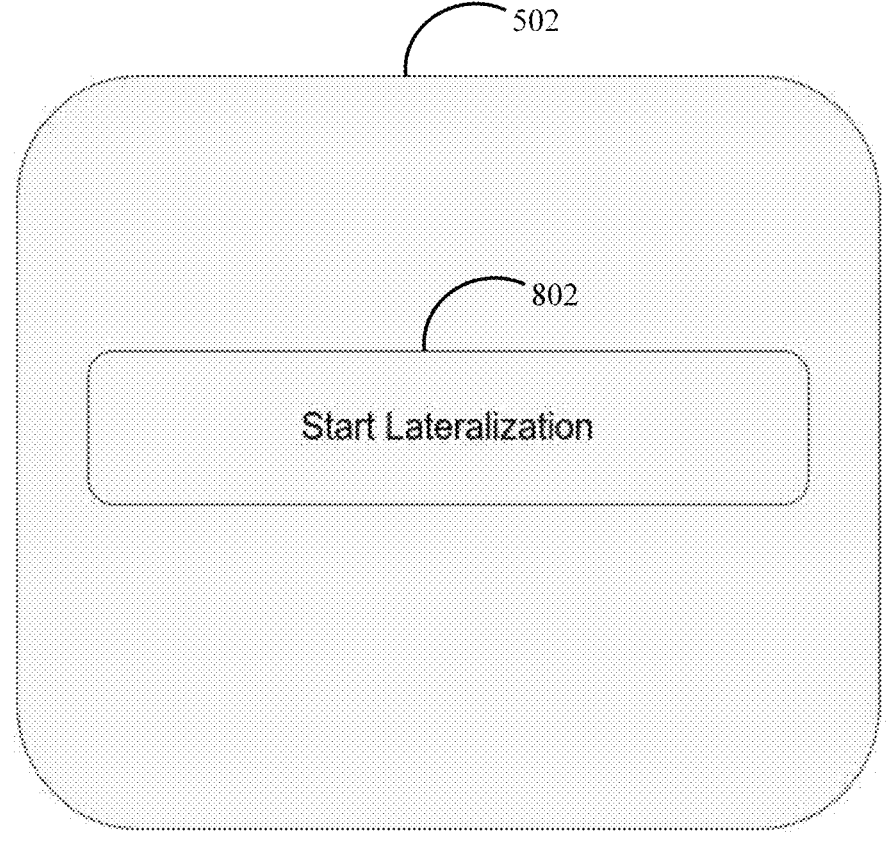
FIG. 7 illustrates a block diagram showing the UI, which facilitates the surgeon to start lateralization in the SCS system, according to an embodiment.

It should be noted that the SCS electrode 110 may be hooked in the base unit 204, i.e., the device and the recording electrodes 112 are hooked into the SCS system 200. After that, the surgeon 106 may start lateralizing the SCS electrode 110 to position the SCS electrode 110 in the patient's body. It should be noted that the surgeon 106 may confirm that all inputs and outputs are hooked up. In one embodiment, the surgeon 106 may initiate the lateralization by selecting a start lateralization button 802 in the UI 502 of the SCS system 200, as shown in FIG. 7. Successively, the surgeon 106 may initiate the lateralization after measuring the impedances of the recording electrode 112. The surgeon 106 may determine the SCS electrode 110 area used to stimulate, such as but not limited to "middle" or "top right," which depends on the type of SCS electrode 110 placed. In an exemplary embodiment, the type of SCS electrode 110 may vary from single column leads to multi-column paddle electrodes. In another exemplary embodiment, the SCS electrode 110 may have a bipolar configuration with a single cathode and anode. Successively, surgeon 106 may adjust SCS electrode 110 positioning to optimize left/right symmetry and/or cover localized areas of pain in the patient's body. It can be noted that data related to lateralization of the SCS electrode 110 may be represented by FIG. 8A, FIG. 8B, and FIG. 8C.

Figure 8A:
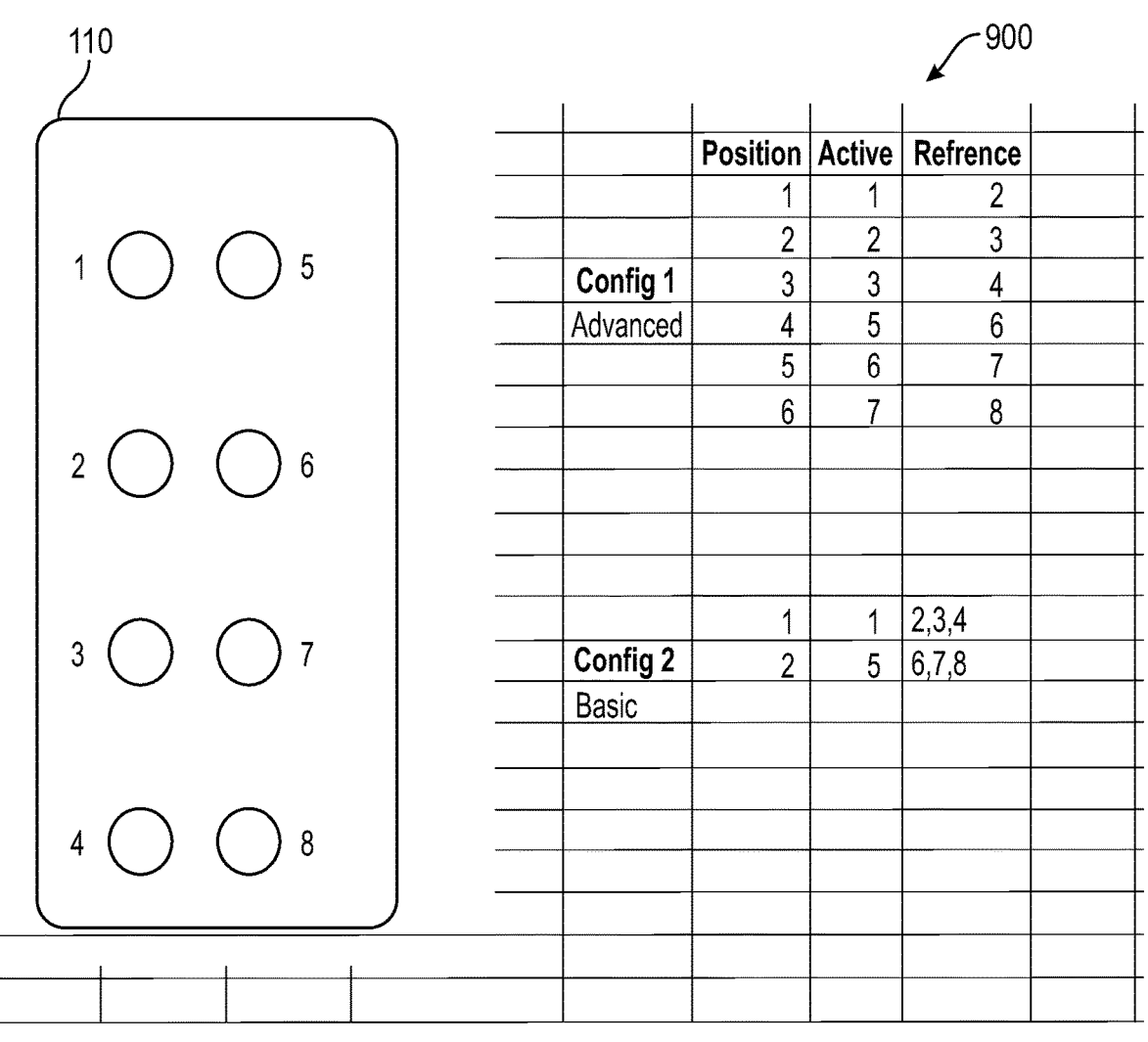
FIG. 8A illustrates a diagram showing a datasheet related to lateralization of the SCS electrode, according to an embodiment.

FIG. 8A, FIG. 8B, and FIG. 8C show datasheets 900, 910, and 920, respectively, related to lateralization of the SCS electrode 110 collected and stored in the SCS system 200. The data may correspond to SCS electrode 110 positioning data. It can be noted that datasheet 900 may represent an example of SCS electrode 110 configuration data. Further, datasheet 910 may represent the EMG data after interpretation. Further, datasheet 920 may represent final data with the position of the SCS electrode 110. In an exemplary embodiment, the SCS electrode 110 is midline. Further, during pre-clinical trials, the SCS system 200 may facilitate storage and retrieval of stimulation data collected corresponding to the patient's body-specific spinal cord. Such data may include, at least but not limited to, EMG results, SCS electrode 110 positioning data, stimulation parameters, and pain-related data.

Figure 9A:
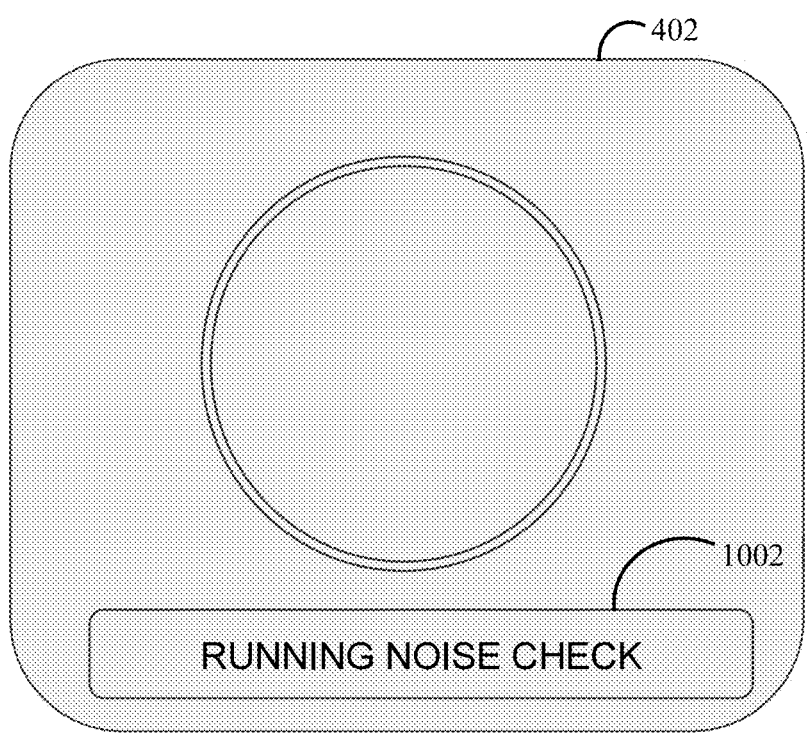
FIG. 9A illustrates a block diagram showing the UI, which illustrates the UI 502 corresponding to an algorithm, of the algorithm module, for checking noise in EMG data, according to an embodiment.

FIGS. 9A-9D illustrate the UI 502 corresponding to an algorithm, of the algorithm module 206, for checking noise in EMG data received from the patient's body. In one embodiment, once the algorithm for checking noise begins, a status corresponding to noise check running may be displayed at a first button 1002 of the UI 502, as shown in FIG. 9A. Further, the algorithm may perform a series of checks based on the frequency of noise/amplitude of noise in the EMG data. Based on the frequency and amplitude of the noise, the SCS system 200 may apply a set of filters to clean or remove noise from the EMG data. It can be noted that the algorithm may apply standard filters to clear intraoperative noise. In one embodiment, the SCS system 200 may detect predefined noise profiles. Further, the SCS system 200 may determine if the SCS system is too noisy. In one embodiment, the algorithm may detect noise profiles using artificial intelligence (AI) technology.

Further, to remove the noise from the EMG data, the SCS system 200 may use any noise removal techniques without departing from the scope of the disclosure. In one embodiment, the noise removal techniques may include but are not limited to, using a low pass differential filter, using an adaptive noise cancellation, and signal filtering based on wavelets of the EMG data. The low pass differential filter may be implemented in the time domain as $$y_k = \sum_{n=1}^{N} (x_{k+n} - x_{k-n}),$$

where $x_k$ is the discrete input time series and $y_k$ is the filtered output. N is the window width. This N is used to adjust the cut-off frequency. The adaptive noise cancellation technique may be used to adaptively reduce the effect of noise on the signal to obtain the desired signal. Further, 50 Hz and 150 Hz components signals may be localized on a frequency band of the EMG signal. In addition, the signal filtering based on wavelets may be used for noise removal from the corrupted signal. Further, denoising of the signal may involve signal decomposition, detail coefficient thresholding, and signal reconstruction. In signal decomposition, both a wavelet prototype and decomposition level (N) may be selected, and the wavelet prototype and the decomposition level (N) may be performed.

Figure 9B:
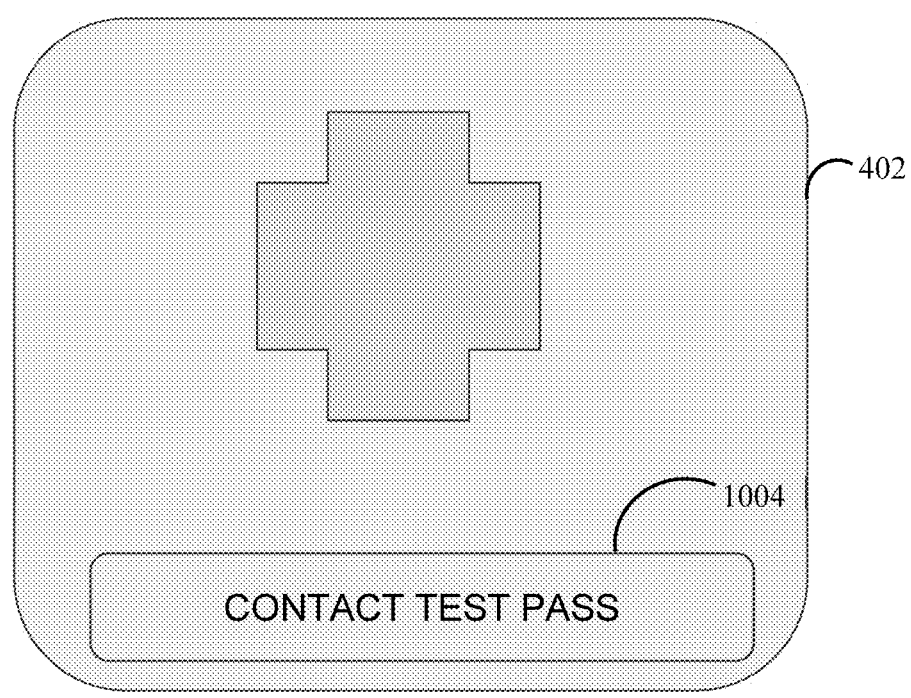
FIG. 9B illustrates a block diagram showing the UI, which illustrates the UI 502 corresponding to an algorithm, of the algorithm module, for checking noise in EMG data, according to another embodiment.
Figure 9C:
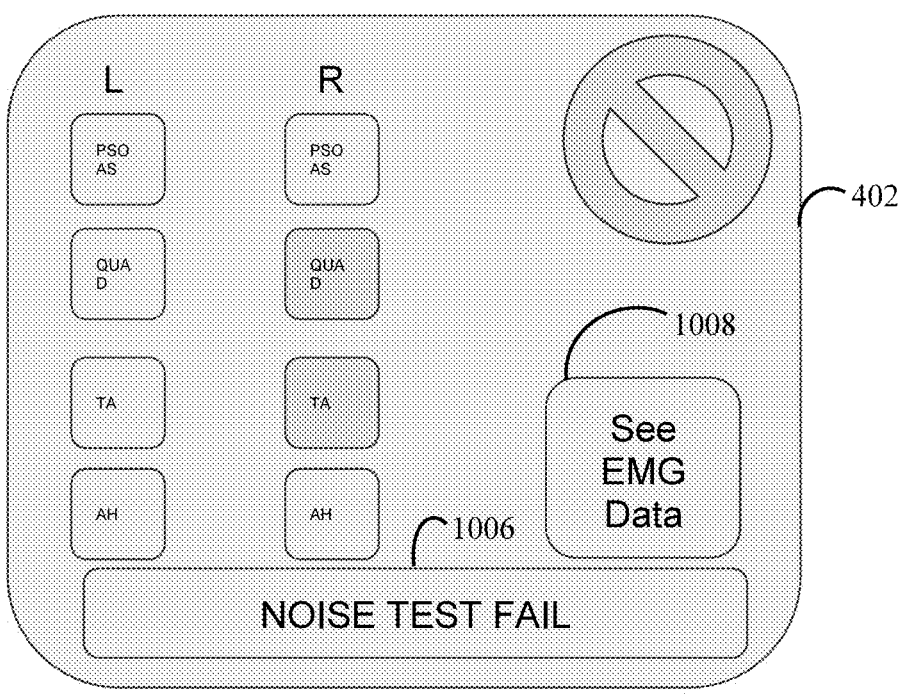
FIG. 9C illustrates a block diagram showing the UI, which illustrates the UI 502 corresponding to an algorithm, of the algorithm module, for checking noise in EMG data, according to another embodiment.
Figure 9D:
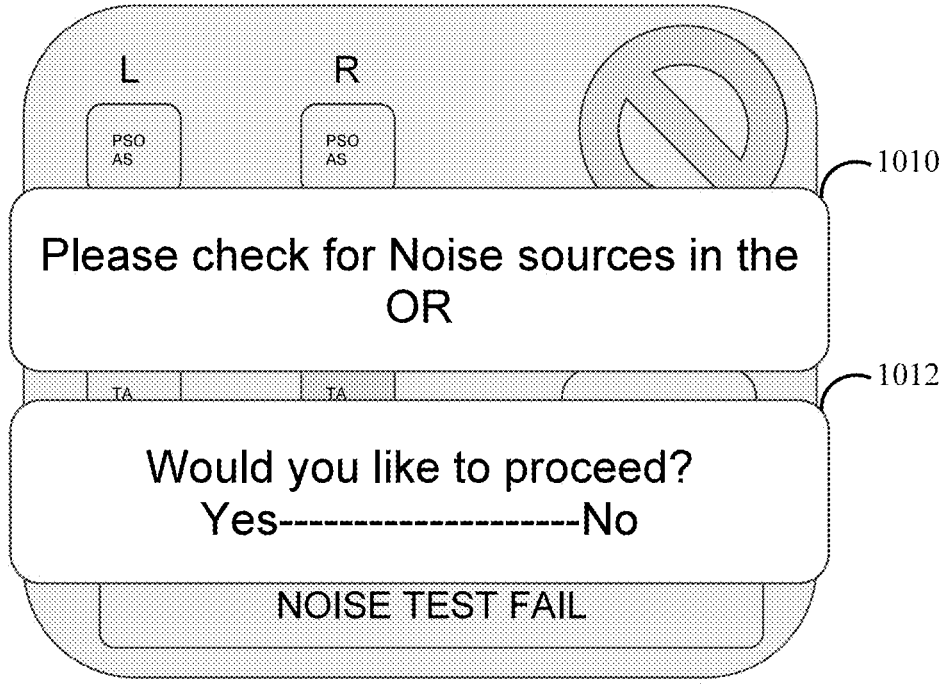
FIG. 9D illustrates a block diagram showing the UI, which illustrates the UI 502 corresponding to an algorithm, of the algorithm module, for checking noise in EMG data, according to another embodiment.
Figure 10:
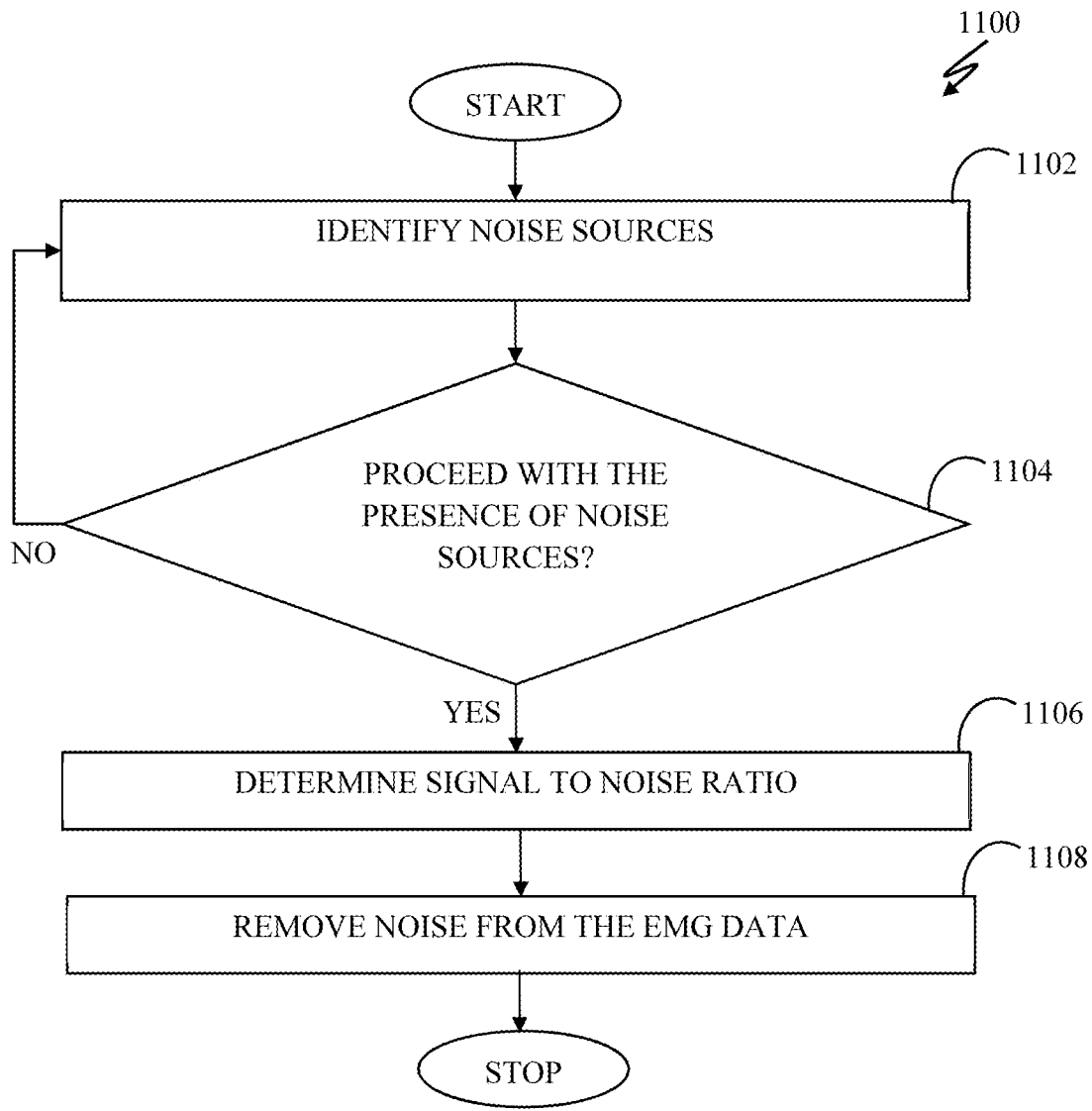
FIG. 10 illustrates a flowchart showing for checking the noise in the EMG data, according to an embodiment.

It can be noted that while using the combination of the noise removal techniques, the SCS system 200 may use results from different noise removal techniques and map the best approach and the order of techniques for each recording electrode 112. In one case, when the SCS system 200 successfully removes the noise, a contact test pass status may be displayed at a second button 1004 of the UI 502, as shown in FIG. 9B. Thus, the UI 502 may display the next step. When the SCS system 200 fails to remove the noise from the EMG data, a noise test fails status may be displayed at a third button 1006 of the UI 502, as shown in FIG. 10C. Further, when the noise test fails, it may identify which EMG channel is too noisy. In addition, the surgeon may be able to monitor the raw EMG data by using a fourth button 1008 of the UI 502, as shown in FIG. 10C. Thus, facilitating the surgeon 106 with the type of noise that exists in the SCS system 200. Further, the UI 502 may use a color system to display the noise types. In one embodiment, red color may indicate bad noise, and yellow may indicate an impact on the EMG signal. The green color may indicate no effect on the EMG data. It can be noted that the UI 502 may display information related to the eight channels of the eight-channel machine, as shown in FIG. 9C. Further, the UI 502 may prompt notification to check for noise sources, as shown by 1010. Further, the UI 502 may also display an option to proceed after the noise fail status, as shown by 1012 of the UI 502. It can be noted that the surgeon 106 may either select to proceed with the process or may deny proceeding, based on the noise fail status. Further, the muscles from which the noise is generated may be let out, and only remaining or available sensors may be used. Further, FIG. 9A, FIG. 9B, FIG. 9C, and FIG. 9D are explained in conjunction with FIG. 10.

FIG. 10 illustrates a method 1100 for checking the noise in the EMG data, according to an embodiment. It should also be noted that in some alternative implementations, the functions noted in the blocks may occur out of the order noted in the drawings. For example, two blocks shown in succession in FIG. 10 may be executed substantially concurrently, or the blocks may sometimes be executed in the reverse order, depending upon the functionality involved. In addition, the process descriptions or blocks in flow charts should be understood as representing decisions made by a hardware structure such as a state machine. The flowchart 1100 starts at step 1102 and proceeds to step 1108. At first, the SCS system 200 may identify the noise sources associated with the EMG data at step 1102. Further, the SCS system 200 may determine whether the surgeon 106 wants to proceed with the presence of noise sources at step 1104. In one case, when the SCS system 200 does not proceed with the presence of noise sources, the SCS system 200 may move to step 1002 to continue identifying noise sources. In another case, when the SCS system 200 proceeds with the presence of noise sources, the SCS system 200 may move to step 1106 to determine a signal-to noise ratio of the EMG data. Based on the determined signal-to-noise ratio, the SCS system 200 may remove the noise from the EMG data at step 1108. It should be noted that the noise may be removed by using one or more filtering techniques such as, but not limited to, low pass differential filter, adaptive noise cancellation, and signal filtering based on wavelets of the EMG data.

Figure 11:
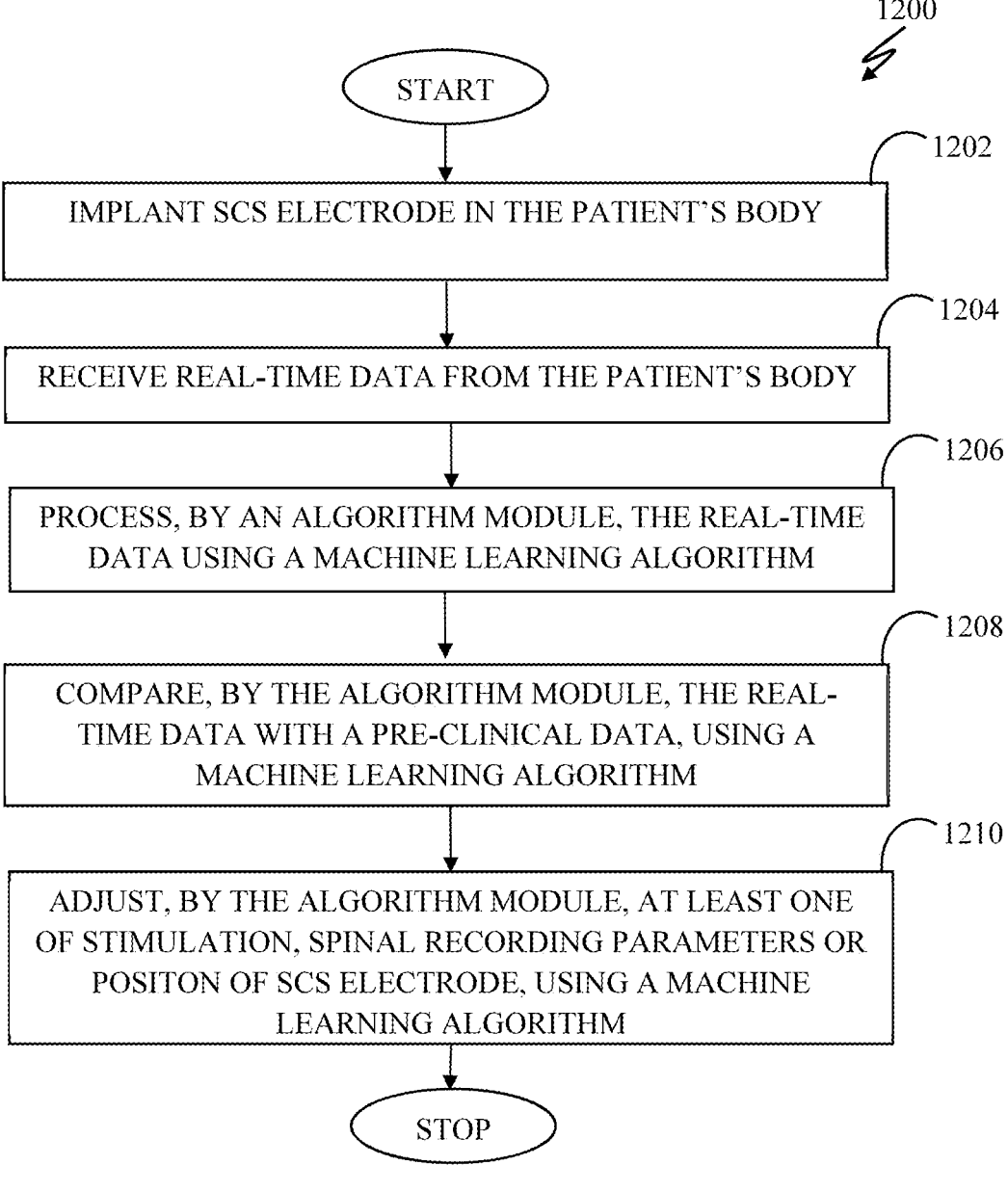
FIG. 11 illustrates a flowchart showing for optimizing the position of the SCS electrode in the patient's body, using ML algorithm, according to an embodiment.

FIG. 11 illustrates a flowchart 1200 showing for optimizing the position of the SCS electrode 110 in the patient's body. It should also be noted that in some alternative implementations, the functions noted in the blocks may occur out of the order noted in the drawings. For example, two blocks shown in succession in FIG. 11 may be executed substantially concurrently, or the blocks may sometimes be executed in the reverse order, depending upon the functionality involved. In addition, the process descriptions or blocks in flow charts should be understood as representing decisions made by a hardware structure such as a state machine. The flowchart 1200 starts at step 1202 and proceeds to step 1210.

At step 1202, the surgeon 106 may implant SCS electrode 110 in the patient's body. Further, using recording electrodes 112, at step 1204, the SCS system 200 may receive real-time data related to the patient's body. It can be noted that the real-time data may include electromyography (EMG) data and compound muscle action potential (CMAP) signals. Further, at step 1206, an algorithm module 206 may process the patient's body's real-time data using a machine learning (ML) algorithm or neural networks and artificial intelligence (AI) model. For example, a supervised machine learning model may be trained on a historical database 207 of previous patients. The model may be fed patient medical record data, along with spinal recording parameters, stimulation parameters, EMG, and CMAP data. A supervisor may indicate desired EMG and CMAP data and the machine learning model may identify characteristics by which cohorts of similar patients can be created who had a positive response to specific spinal recording parameters, and/or stimulation parameters. Once the model is trained, it may be re-run against the database with each new data point. The correlations between spinal needle and stimulation parameters, and the EMG/CMAP data may be calculated based on the patient cohorts identified by the machine learning model. This process will allow the correlations to verify/invalidate/improve the cohorts created by the machine learning model. The processed data may be compared, at step 1208, by the algorithm module 206, with pre-clinical data using the ML algorithm. The pre-clinical data may include EMG results, SCS electrode 110 positioning data, stimulation parameters, and pain-related data. The SCS system 200 may adjust, at step 1210, at least one of the stimulation parameters of the SCS electrode 110 or spinal recording parameters, or position of the SCS electrode 110, based at least on the comparison, using the ML algorithm. Such usage of the ML algorithm may predict and optimize the suggestions, change in stimulation parameters and spinal recording parameters (e.g., needle type or orientation), to be displayed at the display device 210, for the surgeon 106. Recording parameters may include needle type, orientation, etc.

Figure 12A:
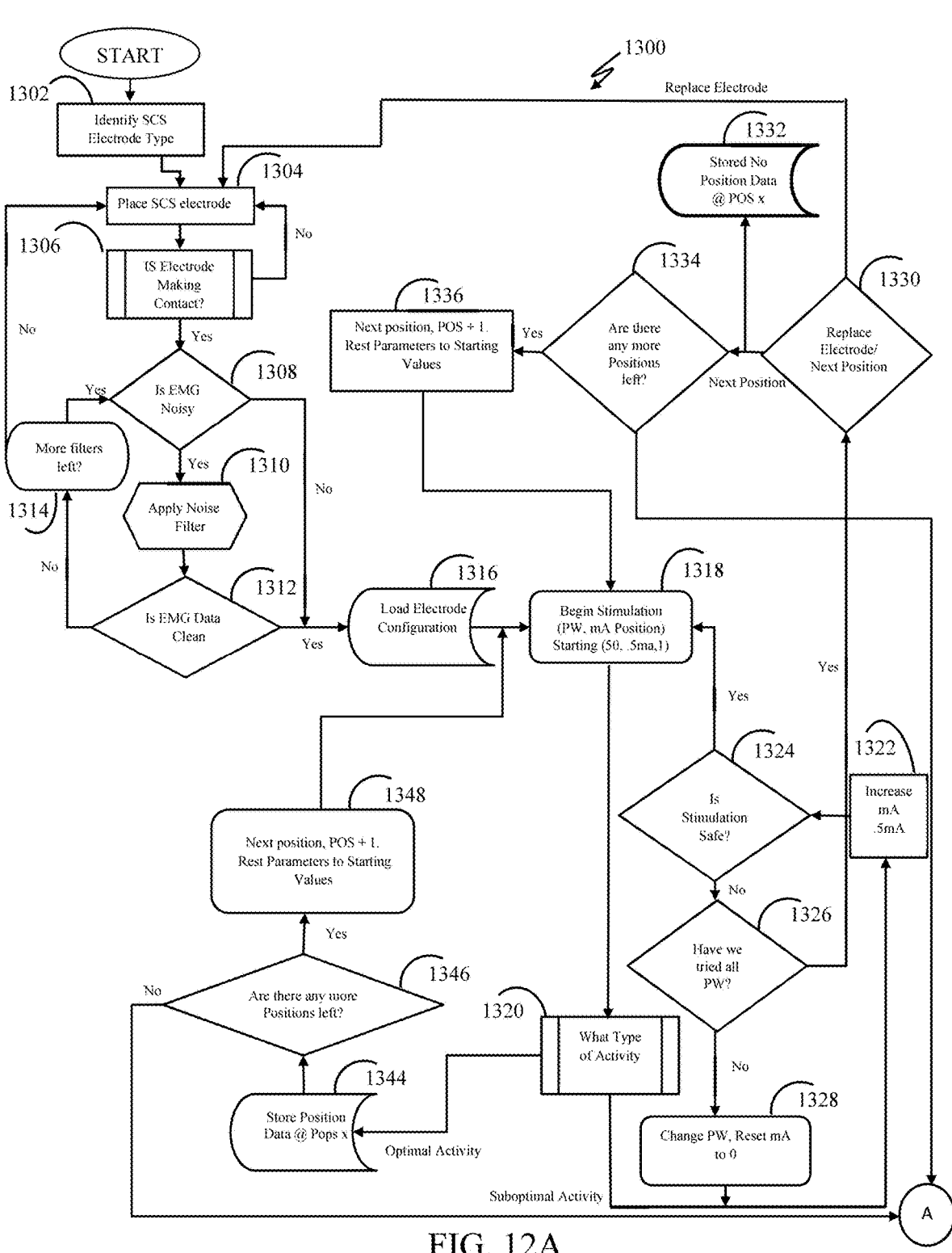
FIG. 12A illustrate a flow chart showing a method of operation of the SCS system, according to an embodiment.
Figure 12B:
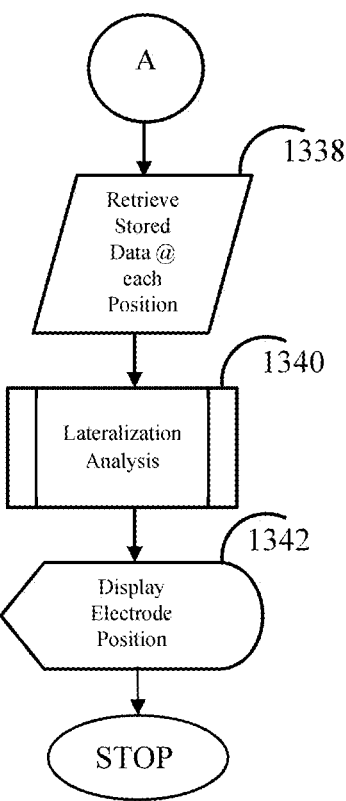
FIG. 12B illustrate a flow chart showing a continued method of operation of the SCS system, according to an embodiment.

The flowchart 1300 of FIGS. 12A and 12B show a method of operation of the SCS system 200, according to an embodiment. It should also be noted that in some alternative implementations, the functions noted in the blocks may occur out of the order noted in the drawings. For example, two blocks are shown in succession in FIGS. 12A and 12B may be executed substantially concurrently, or the blocks may sometimes be executed in the reverse order, depending upon the functionality involved. In addition, the process descriptions or blocks in flow charts should be understood as representing decisions made by a hardware structure such as a state machine. The flowchart 1300 starts at step 1302 and proceeds to step 1348.

At first, the SCS electrode 110 may be identified at step 1302. In one embodiment, the SCS may identify the SCS electrode 110 based on the configuration of the SCS electrode 110, such as but not limited to 2×6, 1×6, and 1×4. Post identification, the SCS electrode 110 may be placed at the spinal cord of the patient's body, at step 1304. The algorithm module 206 may successfully check if the SCS electrode 110 is contacting the spinal cord at step 1306. In one case, based on the checking, if the SCS electrode 110 is not making any contact with the spinal cord, then the algorithm module 206 may execute step 1304 of placing the SCS electrode 110 at the spinal cord of the patient's body. In another case, when the SCS electrode 110 is making contact with the spinal cord, the algorithm module 206 may check if the EMG data is noisy at step 1308. When the EMG data is noisy, the algorithm module 206 may apply a noisy filter on the EM G data at step 1310. Successively, the algorithm module 206 may check if the EMG data is clean, i.e., noise-free, at step 1312. In one case, when the EMG data is still not clean based on the checking, the algorithm module 206 may check if there are any more filters left in the SCS system 200, at step 1314.

Based on the checking, if there are more filters left, the algorithm module 206 may follow steps 1308 to 1312. In another case, if there are no filters left, then the algorithm module 206 may go back to step 1304. As discussed above, at step 1308, when the EMG data is not noisy, the algorithm module 206 may load the SCS electrode 110 configuration at step 1316. Post loading the SCS electrode 110 configuration, the algorithm module 206 may start the stimulation process at step 1318.

The stimulation may start with an initial value of pulse width, current, and position, at step 1318. In an exemplary embodiment, the initial value of pulse width is 50, the current is 5 ma, and the position is 1. Successively, a type of activity may be determined at step 1320. In one embodiment, the type of activity may correspond to a suboptimal activity like compound muscle action potential (cMAP). Successively, the value of current may be increased at step 1322 for a suboptimal activity. In one exemplary embodiment, the value of current is increased by 0.5 mA. After increasing the current value, the safety of stimulation may be checked to determine whether the stimulation is safe or not, at step 1324. In one case, when the stimulation is safe, then the stimulation may be started with the initial value of pulse width, current, and position, at step 1318.

In another case, when the stimulation is not safe, the SCS system 200 may check whether all pulse widths have been tried at step 1326. In one case, when all pulse widths have not been tried, then the value of the pulse width may be changed and resetting the current value to zero, at step 1328. After that, the method may follow step 1322 again to increase the value of current. In another case, when all pulse widths have been tried, then the SCS system 200 may move to the next SCS electrode 110 or indicate replacement of the SCS electrode 110, at step 1330. After placing the SCS electrode 110 in the next position, the SCS system 200 may store the position data at step 1332. Further, the SCS system 200 may check again if any more positions are left at step 1334. In one case, when there are more positions left, the SCS system 200 may change the SCS electrode 110 to the next position while keeping the rest of the parameters at an initial value, at step 1336. After that, the SCS system 200 may again start the process of stimulation at step 1318. In another case, when there are no more positions left, the SCS system 200 may retrieve the stored data regarding each position of the SCS electrode 110, at step 1338. Thus, after retrieving the stored data, the algorithm module 206 may perform the lateralization at step 1340. Finally, the SCS system 200 may display the SCS electrode 110 in the UI 502 of the SCS system 200, at step 1342.

In another case, at step 1320, when the activity is determined to be an optimal activity, the SCS system 200 may store data corresponding with the position of the SCS electrode 110, at step 1344. Further, the SCS system 200 may determine if there are any more positions left for the SCS electrode 110 at step 1346. In one case, when there are positions left for the SCS electrode 110, the SCS system 200 may change the position of the SCS electrode 110 to the next position while keeping the rest of the parameters at an initial value, at step 1348. After that, the SCS system 200 may again start the process of stimulation at step 1318. In another case, when there are no more positions left, the SCS system 200 may retrieve the stored data regarding each position of the SCS electrode 110, at step 1338. Thus, after retrieving the stored data, the algorithm module 206 may perform the lateralization at step 1240. Finally, the SCS system 200 may display the SCS electrode 110 in the UI 502 of the SCS system 200, at step 1342.

The subject disclosure describes a method for using a standalone spinal cord SCS electrode 110 positioning system to visually guide the surgeon 106 in the placement of SCS electrode 110 in real-time based on a display of the position of SCS electrode 110 on the spinal column along with corresponding EMG data at said positions.

It will be appreciated by those skilled in the art that changes could be made to the exemplary embodiments described above without departing from the broad inventive concept thereof. Therefore, it is to be understood that this disclosure is not limited to the particular embodiments disclosed, but it is intended to cover modifications within the spirit and scope of the subject disclosure as disclosed above.

What is claimed is:

1. An electrode positioning system, comprising:
   a pulse generator, the pulse generator configured to generate electrical pulse currents based on a parameter selected from a plurality of parameters;
   a Spinal Cord Stimulator (SCS) electrode, the SCS electrode configured to apply the generated electrical pulse currents at a contact point selected from a plurality of contact points;
   a recording electrode configured to measure a first electrophysiologic signal triggered by application of the generated electrical pulse currents;
   an output device configured to indicate the contact point of the SCS electrode relative to a spinal cord and display parameters related to the recording electrode for an adjustment of the recording electrode based on neurophysiology; and
   a base unit, the base unit having:
   a database, and
   a Machine Learning (ML) application configured to:
      receive the measured first electrophysiologic signal,
      filter the measured first electrophysiologic signal, wherein filtering comprises a combination of filters configured to maximize signal clarity;
      refine the parameter of the SCS electrode for applying the electrical pulse current based on the received first electrophysiologic signal,
      instruct the pulse generator to generate the electrical pulse currents based on the refined parameter at the contact point where the SCS electrode is located,
      receive a measured second electrophysiologic signal that is triggered by the application of the electrical pulse currents at the refined parameter by the SCS electrode, determine a correlation coefficient based on a correlation of data previously stored in the database and the second electrophysiological signal, wherein the data previously stored in the database comprises pre-clinical data associated with at least the SCS electrode and the first and second electrophysiologic signals are associated with measured real-time data, at least one of:

instruct the output device to indicate locations of the SCS electrode where the determined correlation coefficient is above a predetermined threshold such that a location of the SCS electrode can be adjusted, and adjust the parameter of the SCS electrode.

2. The electrode positioning system of claim 1, wherein the Machine Learning (ML) application is further configured to:

compare the determined correlation coefficient with the predetermined threshold;

record the determined correlation coefficient in the database as a relevant data and determine if the contact point of the SCS electrode is at a correct location upon determining that the determined correlation coefficient is greater than the predetermined threshold;

select another parameter from the plurality of parameters by which the electrical pulse currents are applied based upon which the data is retrieved upon determining that the determined correlation coefficient is less than the predetermined threshold;

identify another contact point from the plurality of contact points to place the SCS electrode upon determining that all of the plurality of parameters based on which the determined correlation coefficient of the measured second electrophysiologic signal are compared with the predetermined threshold have been made; and send a notification to the output device to move the SCS electrode to one of indicated locations in which it is determined that the contact SCS electrode is at the correct location.

3. The electrode positioning system of claim 1, wherein the output device comprises a display for displaying the location of the SCS electrode.

4. The electrode positioning system of claim 1, wherein the measured electrophysiological signal is the electromyography (EMG) signal or a Compound Muscle Action Potential (CMAP).

5. The electrode positioning system of claim 1, wherein the base unit further comprises an amplifier, the amplifier configured to amplify the measured electrophysiologic signal.

6. The electrode positioning system of claim 1, wherein the Machine Learning (ML) application is trained based on a previously obtained electrophysiologic signal, the parameter, or the determined correlation coefficient recorded in the database.

7. The electrode positioning system of claim 1, wherein the Machine Learning (ML) application communicates with a processor.

8. The electrode positioning system of claim 2, wherein the Machine Learning (ML) application is further configured to filter the retrieved data from the database.

9. An electrode positioning method, comprising:

positioning a Spinal Cord Stimulator (SCS) electrode at a spinal cord of a patient;

using the electrode positioning system of claim 1, receiving a first electrophysiologic signal, filtering the first electrophysiologic signal, wherein filtering comprises a combination of filters configured to maximize signal clarity;

display parameters related to the SCS electrode for an adjustment of the SCS electrode based on neurophysiology, refining a parameter of the SCS electrode for applying electrical pulse currents based on the received first electrophysiologic signal, instructing a pulse generator to generate the electrical pulse currents based on the refined parameter at the contact point where the SCS electrode is located, receiving a second electrophysiologic signal measured in real time that is triggered by an application of the electrical pulse currents at the refined parameter by the SCS electrode, determining a correlation coefficient based on a correlation of a data previously stored in a database and the second electrophysiological signal, wherein the data previously stored in the database comprises pre-clinical data associated with at least the SCS electrode and the first and second electrophysiologic signals are associated with measured real-time data, at least one of:

instructing an output device to indicate locations of the SCS electrode where the determined correlation coefficient is above a predetermined threshold such that a location of the SCS electrode can be adjusted, and adjust the parameter of the SCS electrode.

10. The electrode positioning method of claim 9, further comprising:

using the electrode positioning system of claim 1, comparing the determined correlation coefficient with the predetermined threshold;

storing the determined correlation coefficient in the database as a relevant data and determining if the contact point of the SCS electrode is at a correct location upon determining that the determined correlation coefficient is greater than the predetermined threshold;

selecting another parameter from the plurality of parameters by which the electrical pulse currents are applied based upon which the data is retrieved upon determining that the determined correlation coefficient is less than the predetermined threshold;

identifying another contact point from the plurality of contact points to place the SCS electrode, upon determining that all of the plurality of parameters based on which the determined correlation coefficient of the measured second electrophysiologic signal are compared with the predetermined threshold have been made; and sending a notification to the output device to move the SCS electrode to one of the indicated locations in which it is determined that the contact SCS electrode is at the correct location.

11. An electrode positioning system, comprising:

a pulse generator, the pulse generator configured to generate electrical pulse currents based on a parameter selected from a plurality of parameters;

a Spinal Cord Stimulator (SCS) electrode, the SCS electrode configured to apply the generated electrical pulse currents at a contact point selected from a plurality of contact points;

a recording electrode configured to measure a first electrophysiologic signal triggered by an application of the generated electrical pulse currents, wherein the first electrophysiologic signal is filtered, wherein filtering comprises a combination of filters configured to maximize signal clarity;

an output device configured to indicate the contact point of the SCS electrode relative to a spinal cord and display parameters related to the recording electrode for an adjustment of the recording electrode based on neurophysiology; and a base unit, the base unit having:

a database, and a Machine Learning (ML) application, wherein the ML application is trained based on the selected parameter and a correlation coefficient based on a correlation of data previously stored in the database and a second electrophysiological signal, wherein the data previously stored in the database comprises pre-clinical data associated with at least the SCS electrode and the first and second electrophysiologic signals are associated with measured real-time data such that at least one of:

a location of the SCS electrode and a parameter of the SCS electrode can be adjusted.

12. The electrode positioning system of claim 11, wherein the output device comprises a display for displaying a location of the SCS electrode.

13. The electrode positioning system of claim 11, wherein the measured electrophysiological signal is an electromyography (EMG) signal or a Compound Muscle Action Potential (CMAP).

14. The electrode positioning system of claim 11, wherein the Machine Learning (ML) application communicates with a processor.

15. The electrode positioning system of claim 11, wherein the Machine Learning (ML) application is trained based on a previously obtained electrophysiologic signal.

16. The electrode positioning system of claim 11, wherein the Machine Learning (ML) application is further configured to filter data retrieved from the database.

\* \* \* \* \*